United States Patent
Sarnow et al.

(10) Patent No.: US 11,612,376 B2
(45) Date of Patent: *Mar. 28, 2023

(54) NON-INVASIVE DETERMINATION OF MUSCLE TISSUE SIZE

(71) Applicant: MuscleSound LLC, Glendale, CO (US)

(72) Inventors: Pierre Sarnow, Littleton, CO (US); Stephen S. Kurtz, Englewood, CO (US); Andrew D. Jackson, Denver, CO (US); Wayne Phillips, Gilbert, AZ (US)

(73) Assignee: MUSCLESOUND, INC., Glendale, CO (US)

( * ) Notice: Subject to any disclaimer, the term of this patent is extended or adjusted under 35 U.S.C. 154(b) by 49 days.

This patent is subject to a terminal disclaimer.

(21) Appl. No.: 17/234,551

(22) Filed: Apr. 19, 2021

(65) Prior Publication Data

US 2021/0236085 A1    Aug. 5, 2021

Related U.S. Application Data

(63) Continuation of application No. 15/730,360, filed on Oct. 11, 2017, now Pat. No. 11,013,490.

(Continued)

(51) Int. Cl.
*A61B 8/08*       (2006.01)
*A61B 8/00*       (2006.01)
(Continued)

(52) U.S. Cl.
CPC .......... *A61B 8/0858* (2013.01); *A61B 8/4427* (2013.01); *A61B 8/4461* (2013.01);
(Continued)

(58) Field of Classification Search
CPC ... G06T 7/136; G06T 7/62; G06T 7/11; G06T 7/155; G16H 50/00; G16H 50/20; G16H 50/30; G16H 20/00; G16H 20/30
See application file for complete search history.

(56) References Cited

U.S. PATENT DOCUMENTS 4,831,527 A    5/1989   Clark
4,876,733 A   10/1989   Lavin
(Continued)

FOREIGN PATENT DOCUMENTS

KR   20130006011         1/2013
KR   20130006011 A   *   1/2013
WO   WO 14/115056        7/2014

OTHER PUBLICATIONS

Hedrick, W. R., and D. L. Hykes. "Image and signal processing in diagnostic ultrasound imaging." Journal of diagnostic medical Sonography 5.5 (1989): 231-239.*

(Continued)

*Primary Examiner* — Carolyn A Pehlke
(74) *Attorney, Agent, or Firm* — Brownstein Hyatt Farber Schreck, LLP

(57) ABSTRACT

Provided is a non-invasive system and method of determining muscle tissue size based on image processing. The method includes receiving at least one ultrasound scan image of at least a portion of a skin layer as disposed above one or more additional tissue layers, the image provided by a plurality of pixels. The method continues by introducing noise into the pixels of the image and thresholding the pixels of the image to provide a binary image having a plurality of structural elements of different sizes. The method continues with morphing the structural elements of the binary image to remove small structural elements and connect large structural elements. With this resulting image, the method distinguishes muscle tissue from remaining elements and determines the muscle tissue size. Associated apparatuses and computer program products are also disclosed.

20 Claims, 14 Drawing Sheets

Related U.S. Application Data

(60) Provisional application No. 62/422,374, filed on Nov. 15, 2016.

(51) Int. Cl.
    *G06T 7/136*     (2017.01)
    *G06T 7/155*     (2017.01)
    *G06T 7/62*     (2017.01)
    *G06T 7/11*     (2017.01)

(52) U.S. Cl.
    CPC .............. *A61B 8/5223* (2013.01); *G06T 7/11* (2017.01); *G06T 7/136* (2017.01); *G06T 7/155* (2017.01); *G06T 7/62* (2017.01); *A61B 8/4227* (2013.01); *A61B 8/4472* (2013.01); *A61B 8/56* (2013.01); *G06T 2207/10132* (2013.01); *G06T 2207/30004* (2013.01)

(56) References Cited

U.S. PATENT DOCUMENTS

| | | | |
|---|---|---|---|
| 5,208,747 A | 5/1993 | Wilson et al. | |
| 5,670,135 A | 9/1997 | Schroder | |
| 5,941,825 A | 8/1999 | Lang et al. | |
| 6,542,250 B1 | 2/2003 | Weber et al. | |
| 6,656,121 B2 | 12/2003 | Jeong et al. | |
| 6,705,994 B2 | 3/2004 | Vortman et al. | |
| 7,658,714 B2 | 2/2010 | Leibig et al. | |
| 7,664,298 B2 | 2/2010 | Lang et al. | |
| 7,683,617 B2 | 3/2010 | Van Zijl et al. | |
| 7,918,794 B2 | 4/2011 | Pineau et al. | |
| 8,068,899 B2 | 11/2011 | Llewellyn et al. | |
| 8,135,179 B2 | 3/2012 | Wilson et al. | |
| 8,351,655 B2 * | 1/2013 | Hwang | G01N 33/12 345/611 |
| 8,512,247 B2 | 8/2013 | Hill | |
| 8,517,942 B2 | 8/2013 | Hill | |
| 8,562,529 B2 | 10/2013 | Hill | |
| 8,715,187 B2 | 5/2014 | Davis et al. | |
| 8,811,745 B2 | 8/2014 | Farsiu et al. | |
| 9,364,179 B2 | 6/2016 | Hill | |
| 9,579,079 B2 | 2/2017 | Jeanne et al. | |
| 9,642,593 B2 | 5/2017 | Sarnow et al. | |
| 10,028,700 B2 | 7/2018 | Sarnow et al. | |
| 10,157,465 B2 | 12/2018 | Sugiyama et al. | |
| 10,327,692 B2 | 6/2019 | Uchiyama | |
| 10,463,346 B2 | 11/2019 | Hill et al. | |
| 11,013,490 B2 * | 5/2021 | Sarnow | G06T 7/62 |
| 2003/0018257 A1 | 1/2003 | Hsu et al. | |
| 2004/0125987 A1 | 7/2004 | Eger et al. | |
| 2004/0131227 A1 | 7/2004 | Bravomalo | |
| 2006/0184024 A1 | 8/2006 | Da Silva et al. | |
| 2007/0016061 A1 | 1/2007 | Da Silva et al. | |
| 2009/0012406 A1 | 1/2009 | Llewellyn et al. | |
| 2009/0264756 A1 | 10/2009 | Da Silva et al. | |
| 2009/0270728 A1 | 10/2009 | Da Silva et al. | |
| 2010/0036246 A1 | 2/2010 | Kushculey et al. | |
| 2012/0116223 A1 | 5/2012 | Da Silva et al. | |
| 2012/0165703 A1 | 6/2012 | Bottum | |
| 2012/0254749 A1 | 10/2012 | Downs, III et al. | |
| 2013/0123629 A1 | 5/2013 | Rosenberg et al. | |
| 2015/0045690 A1 | 2/2015 | Uchiyama | |
| 2015/0374343 A1 | 12/2015 | Shan et al. | |
| 2017/0035352 A1 | 2/2017 | Appleby | |
| 2017/0046837 A1 | 2/2017 | Leinhard | |
| 2018/0132817 A1 | 5/2018 | Sarnow et al. | |
| 2018/0146947 A1 | 5/2018 | Sarnow et al. | |
| 2018/0214118 A1 | 8/2018 | Sarnow et al. | |
| 2018/0249946 A1 | 9/2018 | Sarnow et al. | |
| 2021/0378587 A1 | 8/2021 | Sarnow et al. | |
| 2021/0321979 A1 | 10/2021 | Sarnow et al. | |
| 2021/0338196 A1 | 11/2021 | Sarnow et al. | |

OTHER PUBLICATIONS

Definition of Sleek, Merriam-Webster dictionary online; downloaded Aug. 11, 2022.*

Costill et al., "Muscle glycogen utilization during prolonged exercise on successive days," *Journal of Applied Physiology*, 1971, vol. 31, No. 6, pp. 834-838.

Definition of "doubling," https://www.thefreedictionary.com/doubling, retrieved on Jan. 28, 2021.

Elamaran et al., "A Case Study of Impulse Noise Reduction Using Morphological Image Processing with Structuring Elements," *Asian Journal of Scientific Research*, vol. 8, No. 3, 2015, pp. 291-303.

Fisher et al., "Spatial Filters—Gaussian Smoothing," https://homepages.inf.ed.ac.uk/rbf/HIPR2/gsmooth.htm, Apr. 24, 2020, 9 pages.

Gabriel et al., "Ultrasound of the abdomen in endurance athletes," *Eur J Appl Physiol*, 1996, vol. 73, pp. 191-193.

Jackson et al., "Practical Assessment of Body Composition," *Physicians Sports Medicine*, 1985, vol. 13, pp. 76-90.

Kadah et al., "Classification Algorithms for Quantitative Tissue Characterization of Diffuse Liver Disease from Ultrasound Images," *IEEE Transactions on Medical Imaging*, 1996, vol. 15, No. 4, pp. 466-478.

Koda et al., "Sonographic subcutaneous and visceral fat indices represent the distribution of body fat volume," *Abdominal Imaging*, 2007, vol. 32, pp. 387-392.

Leahy et al., "Ultrasound Measurement of Subcutaneous Adipose Tissue Thickness Accurately Predicts Total and Segmental Body Fat of Young Adults," *Ultrasound in Medicine and Biology*, 2012, vol. 38, No. 1, pp. 28-34.

MathWorks Announces Release 2014a of the MATLAB and Simulink Product Families, https://www.mathworks.com/company/newsroom/mathworks-announces-release-2014a-of-the-matlab-and-simulink-product-families.html, Mar. 7, 2014, 6 pages.

Nguyen et al., "Contrast-Enhanced Ultrasonography in Patients with Glycogen Storage Disease Type Ia and Adenomas," *Journal of Ultrasound Medicine*, 2009, vol. 28, pp. 497-505.

Price et al., "Effect of muscle glycogen content on exercise-induced changes in muscle T2 times," *Muscle Glycogen, Exercise, and T2 Times*, 1998, pp. 1178-1184.

Salvi, "Architectural Analysis of Musculoskeletal Ultrasound Images," Politecnico di Torino, Dec. 2014, 61 pages.

Steensberg et al., "Muscle glycogen content and glucose uptake during exercise in humans: influence of prior exercise and dietary manipulation," *Journal of Physiology*, vol. 541.1, 2002, pp. 273-281.

The University of Auckland, "Gaussian Filtering," May 25, 2010, 15 pages.

Wagner, "Ultrasound as a Tool to Assess Body Fat," *Journal of Obesity*, vol. 2013, Article ID 280713, 9 pages.

Zhou et al., "Automatic measurement of pennation angle and fascicle length of gastrocnemius muscles ultrasound imaging," Ultrasonics, vol. 57, 2015, pp. 72-83.

Kawakami, Y. et al. "Muscle-fiber pennation angles are greater in hypertrophied than in normal muscles" (1993) J. Appl. Physiol. 74(6) 2740-2744.

Ramsey, J. et al. "Differences in Plantar Flexor Fascicle Length and Pennation Angle Between Healthy and Poststroke Individuals and Implications for Poststroke Plantar Flexor Force Contributions" (2014) Stroke Research and Treatment vol. 2014 6 pages.

Zhou et al., "Dynamic measurement of pennation angle of gastrocnemius muscles during contractions based on ultrasound imaging" (2012) 11:63 10 pages.

Zhu, S. et al., "The correlation of muscle thickness and pennation angle assessed by ultrasound with sarcopenia in elderly Chinese community dwellers" (2019) Clinical Interventions in Aging 14:987-996.

\* cited by examiner

NON-INVASIVE DETERMINATION OF MUSCLE TISSUE SIZE

CROSS-REFERENCE TO RELATED APPLICATIONS

This application is a continuation of U.S. patent application Ser. No. 15/730,360, filed Oct. 11, 2017, which claims the benefit under 35 U.S.C. § 119(e) of U.S. Provisional Patent Application No. 62/422,374, filed on Nov. 15, 2016, the contents of which are incorporated herein by reference as if fully disclosed herein.

FIELD

The described embodiments relate generally to the field of fitness and healthcare and more specifically to non-invasive determination of muscle tissue size.

BACKGROUND

The human body is composed of many types of tissues, not the least of which are bone, muscle, nervous, connective, circulatory and of course muscle tissue. For most people, the amount of certain types of tissues within the body, such as skeletal muscle tissue, can be altered by choices in diet and exercise.

Determination of the size of muscle tissue may be useful for a variety of reasons. For example, professional athletes may use such measurements to adjust a training regimen, such as to maximize muscle tissue size increase for strength, control muscle tissue size increase for speed, and so on. By way of another example, medical professionals may use such measurements for evaluating the safety of treatments for previously bedridden patients who have again become mobile. In yet another example, fitness enthusiasts may use such measurements to ensure that a fitness regimen does not result in imbalanced muscle development.

The most accurate way to determine the size of muscle tissue is through dissection, which is simply not a feasible option for living human beings. Non-invasive methods have been developed, but are generally not accurate. For example, fat mass weight can be calculated and subtracted from total body weight, but this treats muscle tissue the same as organs, skin, bones, and so on. As a result, this is not an accurate way to determine muscle tissue size. Girth measurements can also be taken to monitor muscle tissue size. However, girth measurements also include other tissues such as fat underlying skin. As a result, girth measurement is only a rough guide to muscle tissue size changes. Other methods, such as total weight changes, strength changes, and so on, are also only estimates and are not accurate ways to determine muscle tissue size.

SUMMARY

The present disclosure relates to non-invasive determination of muscle tissue size. At least one ultrasound scan image of at least a portion of a skin layer as disposed above one or more additional tissue layers is received. Noise is introduced into the pixels of the ultrasound scan image. The pixels of the ultrasound scan image are thresholded to provide a binary image having a plurality of structural elements of different sizes. The structural elements of the binary image are morphed to remove small structural elements and connect large structural elements. Muscle tissue is distinguished from remaining structural elements. The muscle tissue size is determined.

In various implementations, a non-invasive method of determining human muscle tissue size includes receiving at least one ultrasound scan image of at least a portion of a skin layer as disposed above one or more additional tissue layers, the ultrasound scan image provided by a plurality of pixels; introducing noise into the pixels of the ultrasound scan image; thresholding the pixels of the ultrasound scan image to provide a binary image having a plurality of structural elements of different sizes; morphing the structural elements of the binary image to remove small structural elements and connect large structural elements; distinguishing muscle tissue from remaining structural elements; and determining the muscle tissue size.

In some examples, one or more systems or apparatuses may perform this method. In various examples, the method is repeated over time upon additional ultrasound scan images to evaluate the muscle tissue size over time.

In numerous examples, distinguishing the muscle tissue further includes evaluating at least a subset of the remaining structural elements. In some cases of such examples, evaluating at least a subset of the remaining structural elements includes determining, for each element, one or more characteristics selected from a group including: area, center of mass, and horizontal length. In various cases of such examples, the muscle tissue is distinguished to be a tissue layer between a topmost generally horizontal white band that is generally horizontally continuous across the binary image and a bottommost generally horizontal white band that is generally horizontally continuous across the binary image.

In some examples, the method further includes imaging a selected portion of a subject's body with an ultrasound device having a movable transducer to provide the ultrasound scan image. In numerous cases of such examples, the determination of muscle tissue size is performed about contemporaneously with the imaging of the subject with the ultrasound device for another purpose.

In some implementations, a non-invasive method of determining human muscle tissue size includes providing an ultrasound device having a movable transducer, the transducer operable in a high frequency range; selecting a target area of a subject; adjusting the ultrasound device for a depth of scan appropriate for the selected target area; disposing the transducer proximate to the subject and perpendicular to the selected target area; scanning the selected target area by processing ultrasound reflection received by the transducer to provide at least a partial scan image of the selected target area, the partial scan image provided by a plurality of pixels; introducing noise into the pixels of the partial scan image; thresholding the pixels of the partial scan image to provide a binary image having a plurality of structural elements of different sizes; morphing the structural elements of the binary image to remove small structural elements and connect large structural elements; distinguishing muscle tissue from remaining structural elements; and determining the muscle tissue size. In some examples, one or more systems or apparatuses may perform this method.

In various examples, the morphing is mathematical morphology. In some examples, the morphing includes applying a morphological function for opening.

In numerous examples, the method includes vertically cropping one or both sides of the partial scan image before introducing noise into a remaining central portion of the partial scan image. In some cases of such examples, between $\frac{1}{10}$ and $\frac{1}{5}$ of the partial scan image is vertically cropped from one or both sides.

In some examples, the method is performed in about real time. In various examples, the method is about contemporaneously performed on different partial scan images from different locations about a subject's body.

In numerous implementations, a non-invasive method of determining human muscle tissue size includes receiving at least one ultrasound scan image of at least a portion of a skin layer as disposed above one or more additional tissue layers, the ultrasound scan image provided by a plurality of pixels; introducing noise into the pixels of the ultrasound scan image; thresholding the pixels of the ultrasound scan image to provide a binary image having a plurality of structural elements of different sizes; morphing the structural elements of the binary image to remove small structural elements and connect large structural elements; distinguishing muscle tissue from remaining structural elements by identifying the muscle tissue as a largest element composed of contiguous pixels having a same value; and determining the muscle tissue size. In some examples, one or more systems or apparatuses may perform this method.

In some examples, the method further includes reporting the muscle tissue size. In numerous examples, the method further includes comparing the muscle tissue size to a muscle tissue size goal. In various examples, the muscle tissue size goal is based on a historic muscle tissue size, muscle tissue sizes of other subjects, comparison of contralateral muscles, a performance objective, and so on.

In numerous examples, determining the muscle tissue size includes determining a center of mass of the muscle tissue in a direction defined as vertical with respect to a horizontal axis defined by the skin layer and doubling the center of mass of the muscle tissue in the direction. In various examples, determining the muscle tissue size includes determining a thickness of a left rectus formoris, a left vastus lateralis, a right rectus formoris, a right vastus lateralis, a bicep, or a hamstring.

BRIEF DESCRIPTION OF THE DRAWINGS

The disclosure will be readily understood by the following detailed description in conjunction with the accompanying drawings, wherein like reference numerals designate like structural elements.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The description that follows includes sample systems, methods, and computer program products that embody various elements of the present disclosure. However, it should be understood that the described disclosure may be practiced in a variety of forms in addition to those described herein.

Before proceeding with the detailed description, it is to be appreciated that the present teaching is by way of example only, not by limitation. The concepts herein are not limited to use or application with a specific system or method for non-invasive determination of muscle tissue size. Thus although the instrumentalities described herein are for the convenience of explanation shown and described with respect to exemplary embodiments, it will be understood and appreciated that the principles herein may be applied equally in other types of systems and methods involving the determination of muscle tissue size and specifically muscle tissue size in humans.

The present disclosure relates to non-invasive determination of muscle tissue size. At least one ultrasound scan image of at least a portion of a skin layer as disposed above one or more additional tissue layers is received. Noise is introduced into the pixels of the ultrasound scan image. The pixels of the ultrasound scan image are thresholded to provide a binary image having a plurality of structural elements of different sizes. The structural elements of the binary image are morphed to remove small structural elements and connect large structural elements. Muscle tissue is distinguished from remaining structural elements. The muscle tissue size is determined.

Figure 1:
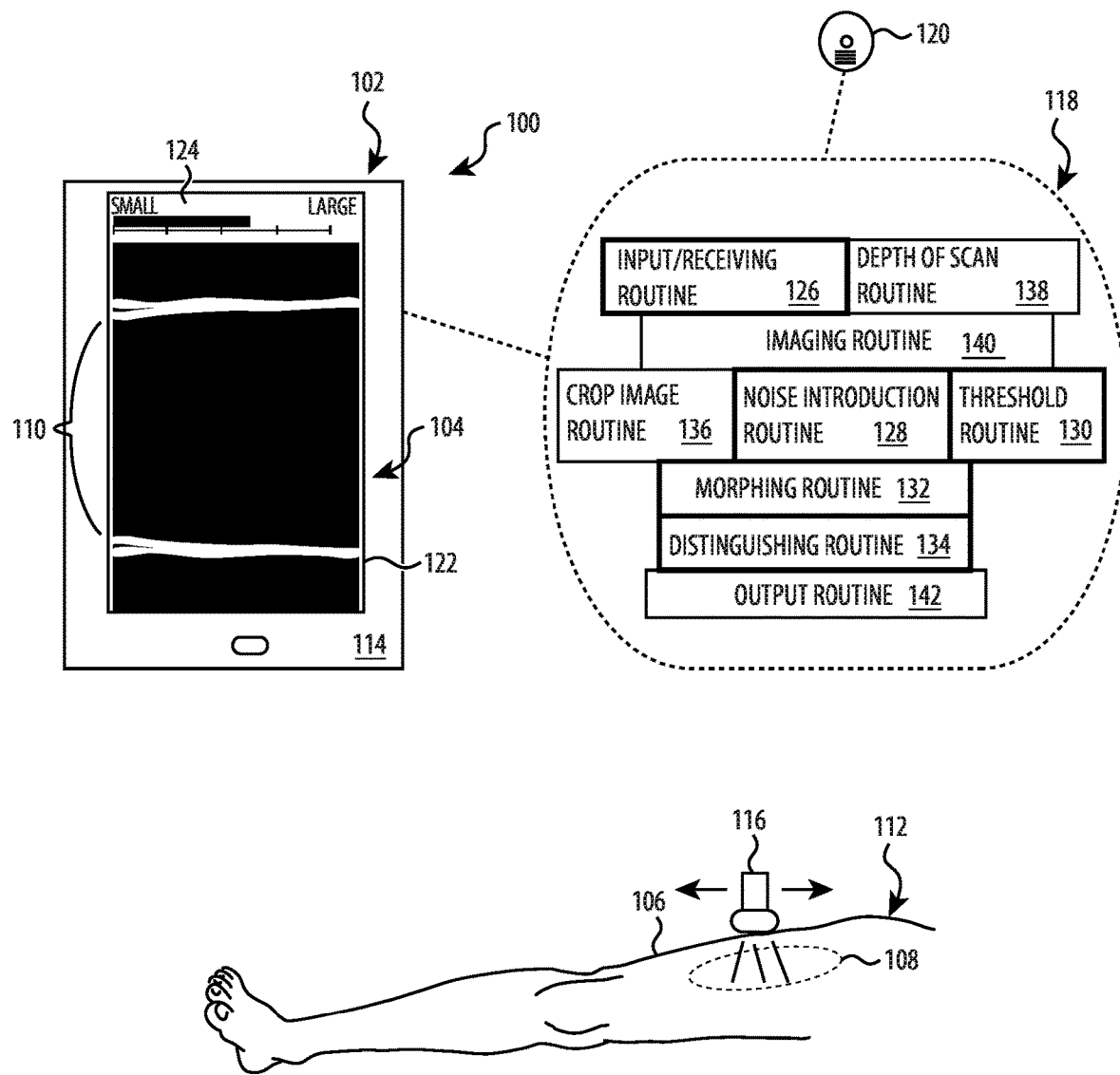
FIG. 1 depicts a high level block diagram of a system for non-invasive tissue evaluation that may be used to determine human muscle tissue size in accordance with at least one embodiment.

Turning to FIG. 1, presented is a high level block diagram of a system for non-invasive tissue analysis (SNTA) 100. For at least one embodiment SNTA 100 is an evaluator 102 structured and arranged to evaluate at least one selected portion of an ultrasound scan image that has undergone image processing, In the present example, the evaluator 102 evaluates an image 104 of at least a portion of a skin layer 106 disposed above one or more additional target tissues 108 to determine a size of muscle tissue 110. More specifically, the evaluator 102 evaluates the image 104 to determine a size of muscle tissue 110 under the skin layer 106.

As used herein, the term "skin" is understood and appreciated for its normal meaning as is expected in the medical profession—namely, an ever-changing organ that contains many specialized cells organized in three generalized layers—the epidermis, the dermis and subcutaneous tissue. Of course each of these layers may also be described as being comprised of multiple layers. With respect to the present disclosure and this description, the skin layer 106 is understood and appreciated to be one or more of the layers of epidermis, dermis and subcutaneous tissue. Precise identification and distinction of these layers may not be necessary for most embodiments. Indeed the identification of the skin layer 106 may serve generally as a point of reference in image 104. Moreover, in varying images, the skin layer 106 may be shown in an image as a portion of the subcutaneous tissue, a portion of the dermis and the subcutaneous tissue, and/or a portion of the epidermis and the dermis and the subcutaneous tissue.

As used herein the term "scan" is understood and appreciated for its normal meaning and as is expected in the medical profession—namely, "a. examination of the body or an organ or part, or a biologically active material, by means of a scanning technique such as ultrasonography—an ultrasound-based diagnostic imaging technique used for visualizing subcutaneous body structures; b. the image so obtained."

With respect to the present disclosure, and as is set forth in greater detail below and in the accompanying figures, the scan image is the element of importance. As such as used herein the terms "scan image," and or "image" are understood to be synonymous. Moreover, the ultrasound transducer provides a signal that for the present disclosure is rendered as an image comprised of a plurality of pixels. The present disclosure teaches the processing and evaluation of the resulting image, and not the processing, evaluation or transformation of the original ultrasound signal or waveform.

In at least one embodiment, SNTA 100 has a processor-enabled device such as computer 114. Computer 114 is adapted to receive the information from the ultrasound transducer 116 and provide a scan image of a portion of a skin layer 106 disposed above one or more additional target tissues 108, of the subject 112. For illustrative purposes the portion shown of the subject 112 is that of the right leg, but as will be further discussed below, SNTA 100 can be, and for at least one embodiment is, applied to multiple different locations of the subject's 112 body.

With respect to FIG. 1, SNTA 100 is at least in part conceptually illustrated in the context of an embodiment for a computer program 118. Such a computer program 118 can be provided upon a non-transitory computer readable media, such as an optical disc 120 or RAM drive that can be provided to a computer 114 to be adapted as SNTA 100. As is further shown and described in connection with FIGS. 10-16, in alternative embodiments the computer program 118 can be provided to a computer serving at least as part of an application providing platform, such as but not limited to the Apple App Store, that platform in turn operable to provide the computer program 118 to a computer 114 to be adapted as SNTA 100.

As will be discussed further below, SNTA 100 may be employed upon a computer 114 having typical components such as a processor, memory, storage devices and input and output devices. During operation, the SNTA 100 may be maintained in active memory for enhanced speed and efficiency. In addition, SNTA 100 may also be operated within a computer network and may utilize distributed resources.

In at least one embodiment, the SNTA 100 system is provided as a dedicated system to provide non-invasive tissue analysis. In at least one alternative embodiment, the SNTA 100 system is achieved by adapting an existing computer 114 which is portable, such as a smart phone (such as an iPhone® or Android®), tablet computer (such as an iPad®), an implant, a wearable device, and so on.

With respect to FIG. 1, SNTA 100 has been conceptually illustrated as a tablet computer 114, having a display 122 operable to display a visual representation of the scan image 104. The display 122 also is shown to provide an indicator 124 to inform an operator of the determined tissue analysis.

For at least one embodiment, the software may be described as including an input/receiving routine 126, a noise introduction routine 128, a threshold routine 130, a morphing routine 132, and a distinguishing routine 134. As is set forth and described below, the elements of SNTA 100 may be summarized for at least one embodiment as follows.

The input/receiving routine 126 is operatively associated with an input devices to receive the scan, such as a Digital Imaging and Communications in Medicine (DICOM) data file, and may also receive other information such as the subject's name, location, current state of exertion, etc. . . . If not in image form, this received scan is provided to the operator as a scan image 104 comprised of a plurality of pixels. The noise introduction 128 is operable to introduce noise into the pixels of the image (such as by horizontal blurring, vertical blurring, other blurring, speckling, and so on). The thresholding routine 130 is operable to threshold each pixel to provide a binary image having a plurality of structural elements of different sizes. The morphing routine 132 is operable to morph elements of the processed image to remove small structural elements and connect large structural elements. The distinguishing routine 134 is operable to distinguish muscle tissue from remaining structural elements and determine the muscle tissue size.

For at least one embodiment, SNTA 100 may also include an optional cropping or crop image routine 136. As has been noted above and will be further understood and appreciated with respect to the following description, the present disclosure advantageously is distinguishing a subject's muscle tissue size through image processing. More specifically image processing techniques including noise introduction (such as by blurring, speckling, and so on), thresholding, and morphing are advantageously combined so as to process a scan image and provide processed image 104 in such a way as to quickly and very accurately distinguish muscle tissue size.

In this respect, for at least one embodiment, between 1/10th and 1/5th of the image is vertically cropped from one or both sides so as to leave a more central portion of the original scan image for subsequent image processing. For at least one alternative embodiment, no cropping is performed.

In addition to the core routines, an input/receiving routine 126, a noise introduction routine 128, a threshold routine 130, a morphing routine 132, and a distinguishing routine 134, in at least one alternative embodiment, SNTA 100 further includes an ultrasound device having a movable transducer 116 operable in a high frequency range and has an adjustable depth of scan. More specifically, the high frequency range may be between about 5 to 20 megahertz. In addition the depth of scan may be between about 1 centimeter and about 7 centimeters. For at least one embodiment, the ultrasound transducer 116 may be an existing commercially available and FDA approved ultrasound transducer 116 incorporated as part of SNTA 100 without departing from the scope of FDA approval for the operation of the ultrasound transducer device.

For at least one embodiment of SNTA 100, the computer program 118 may additionally include a depth of scan routine 138, an imaging routine 140, and optionally an output routine 142. Moreover, the depth of scan routine 138 is operable to adjust the ultrasound device, e.g., ultrasound transducer 116, for a depth of scan appropriate for the target tissues 108. In at least one embodiment, the proper depth of scan is set based on the selection of target tissues 108 as indicated by an operator of SNTA 100.

The imaging routine 140 is operable to direct the movable transducer 116 to scan the selected target tissues 108 by processing ultrasound reflection received by the transducer 116 to provide at least a partial ultrasound scan of the selected target muscle. In at least one embodiment, the imaging routine 140 is structured and arranged to operate with a third party ultrasound imaging software provided to the computer 114.

For at least one embodiment, the optional output routine 142 is operable to output the scan of the target tissues 108 to a storage device, or database. This output routine may also be configured to provide an audible, visual or tactile output to inform the operator of SNTA 100 of the determined muscle tissue size.

With respect to FIG. 1, it is understood and appreciated that the elements, e.g., input/receiving routine 126, noise introduction routine 128, threshold routine 130, morphing routine 132, distinguishing routine 134, crop image routine 136, depth of scan routine 138, imaging routine 140, output routine 142, ultrasound transducer 116 and computer 114 are in at least one embodiment located within a single device. In at least one alternative embodiment, these elements may be distributed over a plurality of interconnected devices. Further, although each of these elements has been shown conceptually as an element, it is understood and appreciated that in varying embodiments, each element may be further subdivided and/or integrated with one or more other elements.

Figure 2:
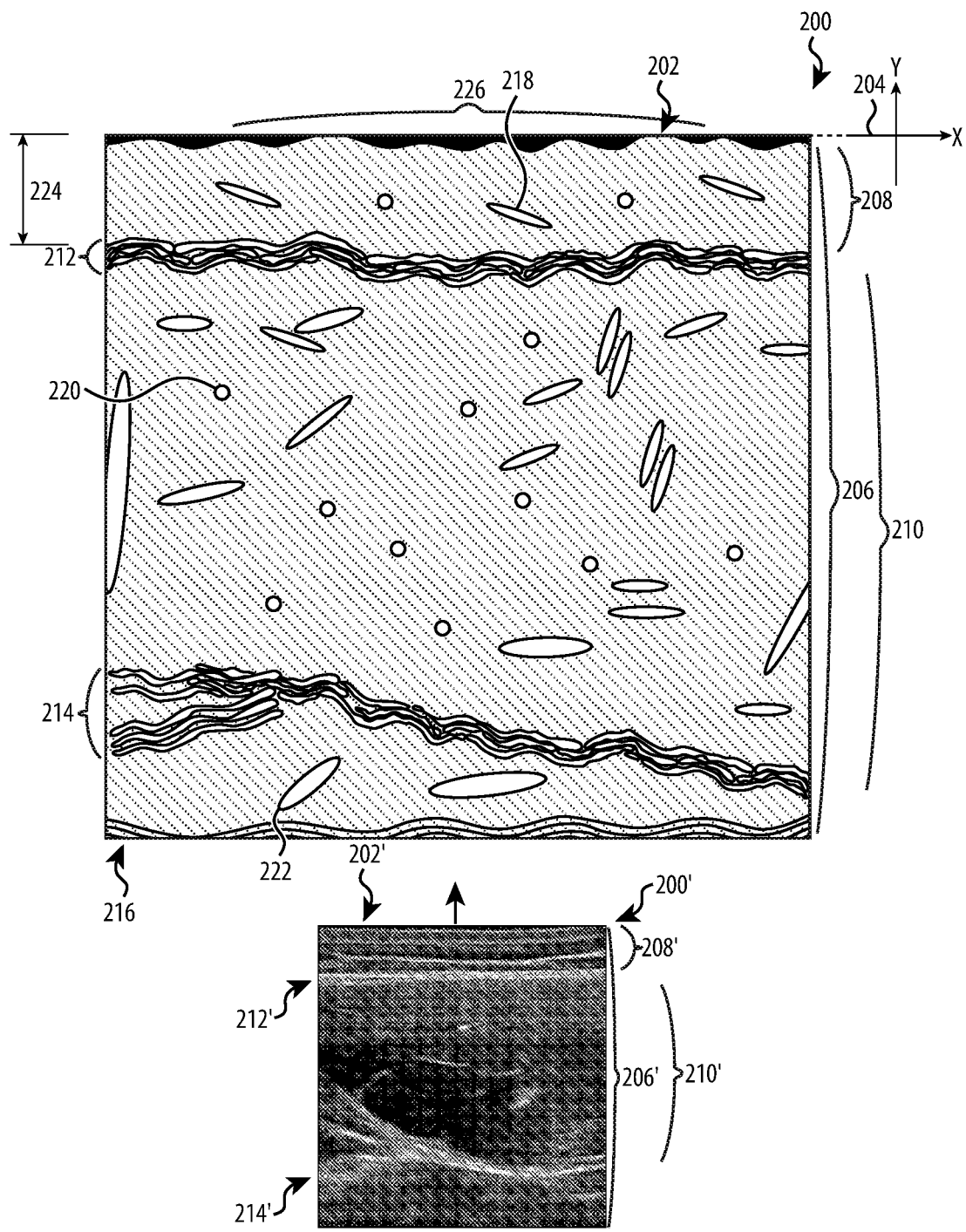
FIG. 2 depicts a conceptual illustration of an ultrasound scan of target tissues in accordance with at least one embodiment.
Figure 3:
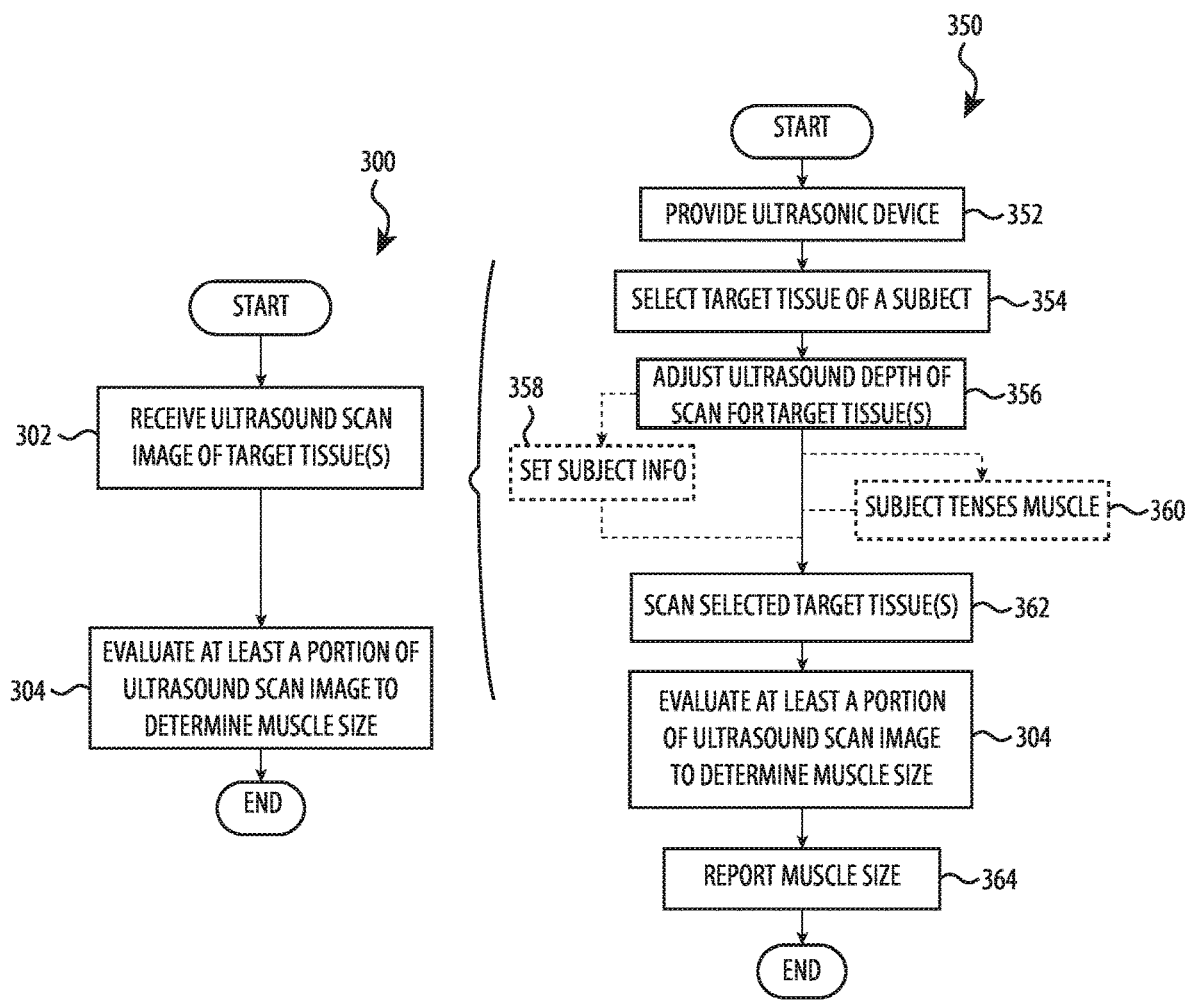
FIG. 3 depicts a high level flow diagram for a method of non-invasive determination of human muscle tissue size in accordance with at least one embodiment.
Figure 4:
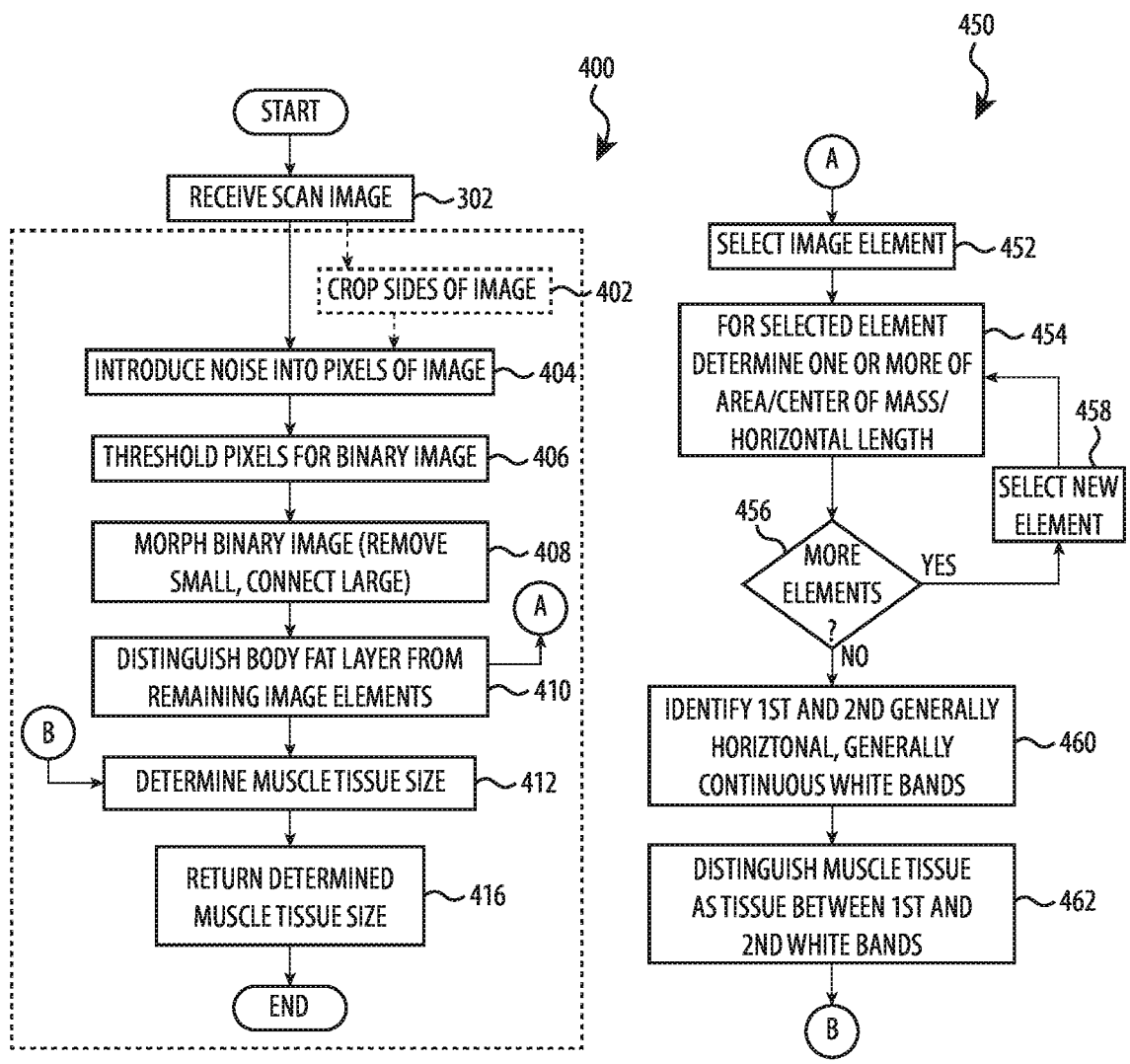
FIG. 4 depicts a refined flow diagram for the evaluating operation for non-invasive determination of human muscle tissue size in accordance with at least one embodiment.

FIGS. 3 and 4 in connection with FIGS. 1, 2 and 5-9 provide a high level flow diagram with conceptual illustrations depicting methods 300, 400, 450 for non-invasive determination of human muscle tissue size in accordance with at least one embodiment. It will be appreciated that the described method(s) need not be performed in the order in which it is herein described, but that this description is merely exemplary of one method of non-invasive determination of human muscle tissue size.

As is shown in FIG. 2, an enlarged conceptual ultrasound scan image 200 is shown corresponding to a real ultrasound scan image 200'. Typically ultrasound scan images such as scan image 200' are rendered in black and white in accordance with a grey scale, though color is certainly an option and within the scope of the present disclosure. Various structures with a subject's body reflect the ultrasound signal with varying intensity. In general there are two distinct patterns of reflection that give rise to the echoes that make up the ultrasound image—specular reflections and scattering reflections.

Specular reflections are responsible for the bright appearances of fibrous structures such as tendons, ligaments and the boundaries between different types of tissues. Scattering gives rise to the characteristic texture of an image seen within soft tissues. The scan image 200' is composed of a plurality of pixels. Scan pixels may correlate directly with image pixels as used to render scan image 200. Of course, in some embodiments the resolution of the scan pixels may be greater than the resolution applied in the scan image, such that each pixel of the scan image may correlate to two or more pixels of the scan.

Those skilled in the art of ultrasound imaging can and often do perceive a great deal of information from images that are otherwise perhaps visually interesting but also perhaps largely unintelligible to the untrained eye.

Through image processing as performed by SNTA 100 and method 300, this training to perceive and differentiate structures within a typical ultrasound image is for all intents and purposes eliminated. For ease of discussion, conceptual rendering of ultrasound images has been provided to ease and facilitate this discussion.

Moreover, as shown in FIG. 2, the scan image 200 may capture a portion of the surface tissue 202, such as the skin at the top of the images, which defines a horizontal axis 204 for the scan image 200. The scan image 200 also shows at least a portion of subcutaneous tissues 206, which likely includes a body fat tissue 208 having a thickness 224, an as yet not clearly delineated area of muscle tissue 210, and other tissues such as fibrous tissues 212 and 214, bone tissue 216 and so on, of which 218, 220 and 222 are exemplary. This same variety of tissues is of course evident in real ultrasound scan image 200', a subset of which have been suggestively identified with like numbers 202', 206'-214'.

Moreover, although scan image 200 provides enough information to discern the presence of body fat tissue 208, muscle tissue 210 and other tissues, these tissues may not be sufficiently distinguished so as to permit accurate determination of muscle tissue size at this point. Indeed, embodiments of the present disclosure may apply image processing techniques so as to clearly distinguish at least the muscle tissue 210 to such a degree that a highly accurate size measurement may be obtained.

As noted above and further described below, for at least one embodiment, between 1/10th and 1/5th of the image is vertically cropped from one or both sides so as to leave a more central portion 226 of the scan image 200 for subsequent image processing. This cropping is more fully illustrated with respect to FIG. 5.

Further, although the illustrations and discussion provided herein for exemplary purposes generally appear to be 2D (two dimensional) images, the system and methods are equally applicable multi-axis ultrasound imaging techniques, such as for example 3D ultrasound.

FIG. 3 provides a high level flow diagram depicting a method 300 for non-invasive determination of muscle tissue size, which is more fully appreciated with respect to FIGS. 2 and 5-9 providing both real and conceptual illustrations of ultrasound scan images as processed in accordance with at least one embodiment. It will be appreciated that the described method, as well as all other subsequent methods and refinements to the disclosed methods need not be performed in the order in which they are herein described, but that the descriptions are merely exemplary of a method or methods that could be performed for non-invasive muscle tissue size determination.

As shown in FIG. 3, method 300 commences with receiving an ultrasound scan image of target tissue(s), block 302. An exemplary scan image such as scan image 200 is shown in FIG. 2. Moreover, even though muscle tissue may be the primary tissue of interest in one setting, for the muscle tissue size to be accurately determined under the present disclosure it may be desirable to distinguish the muscle tissue from other tissues. In addition, as the muscle tissue is captured in ultrasound scans often performed with an intent to image other tissues, such scan images may also be processed under the present disclosure for about real time or later analysis of muscle tissue size. Indeed, substantially real time analysis to determine a subject's muscle tissue size may be performed as a specific procedure, or as a beneficial ancillary procedure when a subject is undergoing an ultrasound imaging process for another purpose (such as determination of glycogen stores, determination of body fat, and so on).

Moreover, scan image 200 may be provided as described above through the use of SNTA 100 in an embodiment providing an ultrasound transducer 116, or through another ultrasound imaging system and/or process. For at least one embodiment the ultrasound scan image is provided by the system(s) and methods as set forth in U.S. Pat. No. 8,562,529 entitled Method and System for Non-Invasive Determination of Glycogen Stores, U.S. Pat. No. 8,517,942 entitled Method for Non-Invasive Determination of Glycogen Stores, U.S. Pat. No. 8,512,247 entitled System for Non-Invasive Determination of Glycogen Stores, U.S. patent application Ser. No. 14/012,538 entitled System and Method for Target Muscle Glycogen Score Determination and Evaluation, and U.S. patent application Ser. No. 14/491,553 entitled System and Method for Non-Invasive Determination of Human Body Fat—each of which is incorporated herein by reference.

With the scan image 200 now received, method 300 continues with the evaluation of at least a portion of the scan image 200 to determine muscle tissue size, block 304. For application of method 300, an embodiment of SNTA 100 need not have, or otherwise be coupled to, an ultrasound transducer 116. Method 300 may also be performed by SNTA 100 when a user desires to review historical data of tissue scans, such as for example to revisit past histories of evaluation to perceive changes in development and potential adjustments to a subject's training methods, general activities, diet or other form of activity and/or medication.

Of course, for real time non-invasive determination of muscle tissue size, in varying embodiments SNTA 100 may indeed include an ultrasound transducer 116 as described above. As such, method 300 may be augmented as method 350, the augmentation as illustrated pertaining to at least one method of providing the received ultrasound scan image 200.

More specifically, for augmented method 350, an ultrasound transducer 116 is provided as part of SNTA 100, block 352. A target tissue, such as a muscle, e.g. target tissue(s) 108, is selected, block 354. As noted, the ultrasound transducer has an adjustable depth for scanning, such as a selection between about 0.5 and 10 centimeters. The ultrasound transducer 116 is adjusted to provide a depth of scan appropriate for the selected target tissue, block 356.

In at least one embodiment, the depth of scan is adjusted manually, such as to about 3.5 centimeters for the skin, body fat, and rectus femoris muscle. In an alternative embodiment, the depth of scan is automatically selected by an operator selecting a desired tissue, such as a muscle tissue, e.g., rectus femoris, vastus lateralis, or biceps. In addition, in varying embodiments, the auto-determined and set depth may also be adjustable by the operator so as to permit adjustment for various body types.

In at least one embodiment additional and optional information about the subject is recorded, as indicated by dotted block 358. This optional information may include, but is not limited to, details such as the subject's name, age, gender, time of day, status of subject—at rest/at VOT Max, after eating, or other such information desired to be recorded and displayed in connection with the scanned image of the target muscle.

Moreover, to summarize for at least one embodiment, the augmented method 350 includes providing an ultrasound device having a movable transducer, the transducer operable in a high frequency range, selecting a target tissue 108 of a subject 112 and adjusting the ultrasound device for a depth of scan appropriate for the selected target tissue 108.

As the ultrasound transducer 116 operates by providing a high frequency signal that is directed into tissue and detecting reflections returned by encountered elements, it is understood and appreciated that the transducer should be aligned generally perpendicular to the selected target muscle. Of course, if a transducer having an alignment configuration that is other than perpendicular is employed, the specific alignment as intended for the transducer should be used.

It is understood and appreciated that an ultrasound transducer 116 may be positioned along the longitudinal or latitudinal axis of the tissue or somewhere in between. For general alignment purposes and ease of operation, in general the operator of the system will select ultrasound transducer 116 alignment matching to either the longitudinal or latitudinal axis of the target tissue 108.

Testing has determined that a key factor for deciding which alignment to use is perhaps the initial quality of the scan image. In other words, for at least one embodiment, at least a longitudinal and a latitudinal image of the target tissues is obtained so that the images can be compared by the operator and/or SNTA 100 to determine which image is best for analysis.

Application of the ultrasound transducer 116 against the subject's skin can be a practiced skill, for if too much pressure is applied the transducer may inadvertently compress the tissue and thereby hamper the quality of the scan and the resulting evaluation of muscle tissue size. However, an easy solution presents itself that substantially minimizes the risk of transducer related compression of the tissue.

As shown by optional dotted block 360, the subject can simply tense his or her muscle if it is the target tissue 108 or directly below the target tissue. More specifically, if the subject acts to tense his or her muscles adjacent to the desired target tissue, the natural action of the muscle contraction causes the muscle to swell and thereby resist compression. The contracted and thereby enlarged muscle may also be advantageous in providing an even clearer cross sectional scan than may be obtained with a relaxed muscle.

In short, while the quality of the scan for the tensed or un-tensed muscle adjacent to the target tissue 108 may be the same for an operator skilled in how much pressure to apply, for the novice, as well as the skilled operator, tensing an adjacent muscle does not appear to significantly hamper the determination of muscle tissue size and may help insure greater consistency of scans in a wide variety of locations and settings. Indeed, for at least one embodiment, when the method of scanning a target tissue(s) 108 is performed, the subject will tense his or her adjacent muscle as a normal and expected part of the scanning process.

Moreover, to achieve the scan of the target tissue 108, the ultrasound transducer 116 is disposed proximate to the target tissue 108 and as the ultrasound transducer 116 is activated the target tissue(s) 108 is scanned, block 362. In at least one embodiment the ultrasound transducer 116 is placed in direct contact with the subject's skin. In at least one alternative embodiment, a protective cover, shield or even the subject's clothing is disposed between the ultrasound transducer 116 and the subject's skin.

A scan image is then provided from the resulting scan, and evaluated as noted above, block 304. A report of the determined muscle tissue size may also be reported, block 364.

In other words, to summarize for at least one embodiment, the augmented method 350 continues with disposing the transducer proximate to the subject 112 and perpendicular to the selected target tissue 108, and then imaging the selected target tissue 108 by processing ultrasound reflection received by the transducer to provide at least a partial scan of the selected target tissue 108. Many ultrasound transducers provide images as cross sections of the tissues and structures whereas others may provide 3-D views. For consistency in analysis, in at least one embodiment the operator of SNTA 100 adopts a convention to scan a target tissue along its long axis or short axis.

For the majority of leg and arm tissues the long axis is generally parallel to bone structure and the short axis is generally perpendicular to bone structure. Indeed in some embodiments, scans with SNTA 100 may be performed substantially contemporaneously along both the long and short axes of a target tissue 108 for enhanced comparison and analysis.

Method 350 then continues with the evaluation of the scan as discussed above with respect to block 304. For at least one embodiment, it is understood and appreciated that the evaluation of the image 104 is performed about contemporaneously with the scanning of the target tissue 108.

The determined muscle tissue size is then reported to the operator, block 364. The determined muscle tissue size may also be recorded for use in plotting the changes in a subject's muscle tissue size over time, and/or in response to various different points of exercise, conditioning, diet, medication and other factors.

FIG. 4 in connection with FIGS. 5-9 provides a high level flow diagram with conceptual illustrations to further refine at least one embodiment of method 300 for evaluating at least a portion of the ultrasound scan image to determine muscle tissue size. Moreover in FIG. 4, method 400 corresponds in greater detail to block 304 of FIG. 3. Again, it is appreciated that the described method need not be performed in the order in which it is herein described, but that this description is merely exemplary of one method for non-invasive determination of human muscle tissue size.

More specifically, as FIG. 4 expands on FIG. 3, initially a scan image of the target tissues 108 is received, block 302.

An exemplary image scan is conveniently provided as scan image 200 as shown and described above with respect to FIG. 2.

Figure 5:
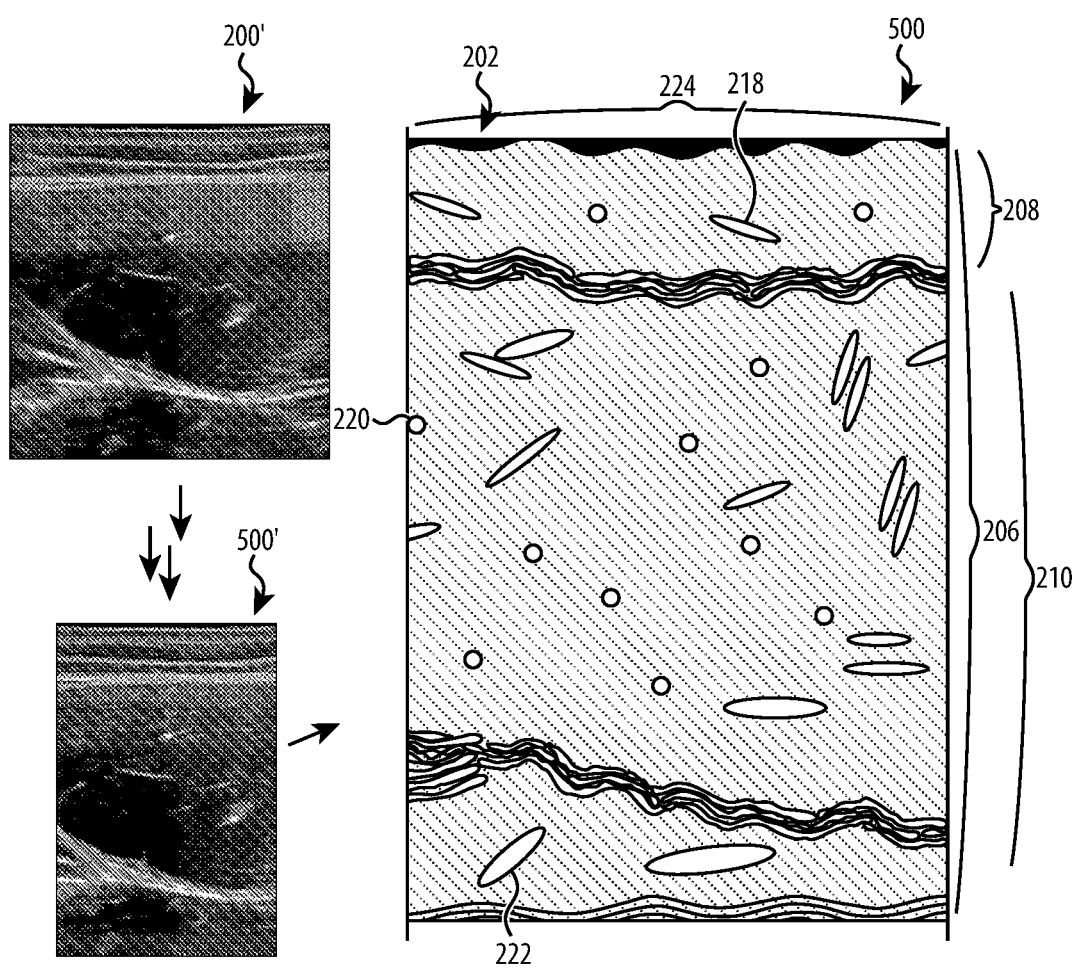
FIG. 5 depicts a conceptual illustration of a cropped ultrasound scan image in accordance with at least one embodiment.

Ultrasound scan images tend to image tissues directly below the transducer most clearly, with the side areas of the scan tending to be less clear. For purposes of subsequent image enhancement, for at least one embodiment one or both sides of the scan image 200 are cropped as is shown in FIG. 5 as cropped scan image 500. Moreover, cropped scan image 500 is the more central portion 226 of scan image 200 shown in FIG. 2. Although embodiments of method 300 may be performed without side cropping, in general between 1/10 and 1/5 of the image is vertically cropped from each side as suggested by dotted lines and optional block 402.

With respect to FIG. 5, as with FIG. 2 above the conceptual cropped scan image 500 is shown to generally corresponding to real cropped ultrasound scan image 500'.

Next, method 400 proceeds to introduce noise into the pixels. For example, the pixels may be horizontally blurred (though they may also be vertically or otherwise blurred, speckled, and so on) as shown in the horizontally blurred scan image 600 shown in FIG. 6, block 404 (see FIG. 4). Again blurred scan image 600 conceptualizes blurred real ultrasound scan image 600'.

Traditionally the clarity of an ultrasound image and indeed the sharpness of the elements within the ultrasound image are very important. This is quite understandable as often times an ultrasound image is used to guide a doctor in surgery, so clear imaging is important for both the doctor and the patient.

For the present disclosure, sharpness of detail within the image may not be important. In fact, the present disclosure teaches how image processing techniques may be applied so as to remove elements of small detail and enhance the ultimate distinguishing of muscle tissue size. In image processing, a kernel such as a convolution matrix, mask or filter is a small matrix that can be applied to propagate a change in a source image for a desired effect. Moreover the change imparted is a result of convolution between an applied kernel and an image.

Blurring is an image processing technique commonly applied so as to reduce and/or introduce noise and reduce detail. Blurring functions are well understood and known to those skilled in the art and need not be discussed in detail here.

A high level discussion of blurring is provided so as to facilitate general understanding of the process so as to further appreciate the advantageous achievement of SNTA 100 and method 300. Although blurring is discussed herein, other techniques such as speckling may be used without departing from the present disclosure. In simple terms blurring an object means that each of the pixels in the source image gets spread over and mixed with surrounding pixels. With respect to the present disclosure, blurring may be achieved by application of a Mean Filter, Weighted Average Filter, Gaussian Filter or other appropriate filter. A Mean Filter is also known as a Box Filter or Average Filter, and is understood to have the following properties—it is odd ordered, the sum of all elements should be 1 and the elements of the filter are the same. A Weighted Average Filter acts as the name implies—giving more weight to the center value. Here again it is odd ordered, the sum of all elements should be 1, but the weight of the center element should be more than all of the other elements. A Gaussian Filter is one that uses a Gaussian function, which also expresses the normal distribution in statistics, for calculating the transformation to apply to each pixel in the image.

For purposes of the present example, blurring is only to be applied along the horizontal axis (though in other examples other blurring and/or other techniques such as speckling may be used). As such a 1×3 Mean Filter or a one dimension Gaussian Function is typically appropriate. For at least one embodiment, the blurring filter is a 1 dimensional Gaussian function:

$$G(x) = \frac{1}{\sqrt{2\pi\sigma^2}} e^{-\frac{x^2}{2\sigma^2}}$$

For at least one alternative embodiment, a 1×3 Mean Filter such as [⅓, ⅓, ⅓] is applied.

Figure 6:
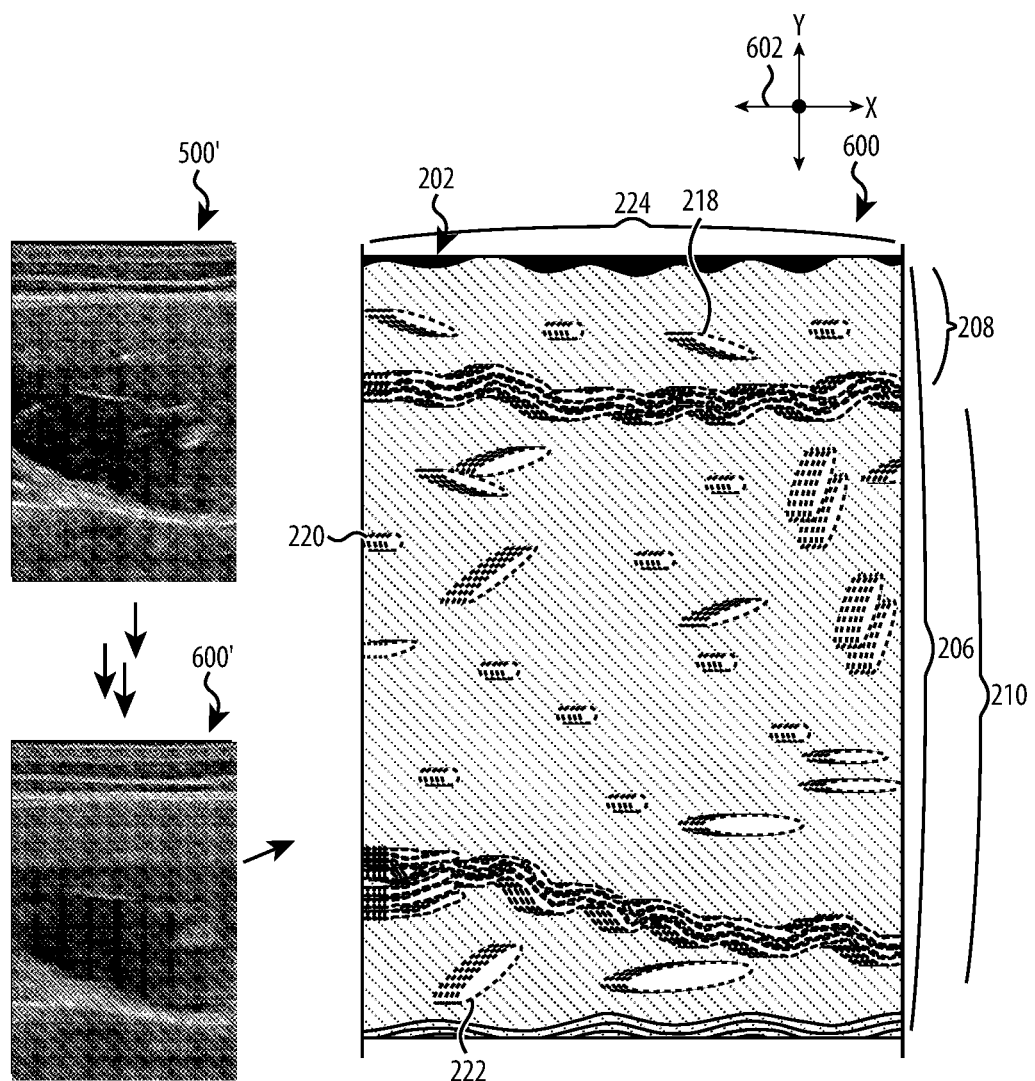
FIG. 6 depicts a conceptual illustration of a horizontally blurred ultrasound scan image in accordance with at least one embodiment.

As is shown in FIG. 6, in conceptually blurred image 600, the tissue elements such as 222 and 224 have been blurred along the horizontal X axis as indicated by coordinate axis 602. No blurring has occurred along the vertical Y axis. As such the edge distinctions along the horizontal axis are less sharp as blurring makes the collections of similar pixels either bigger or smaller. And again, conceptual blurred image 600 corresponds generally to real blurred image 600'.

Figure 7:
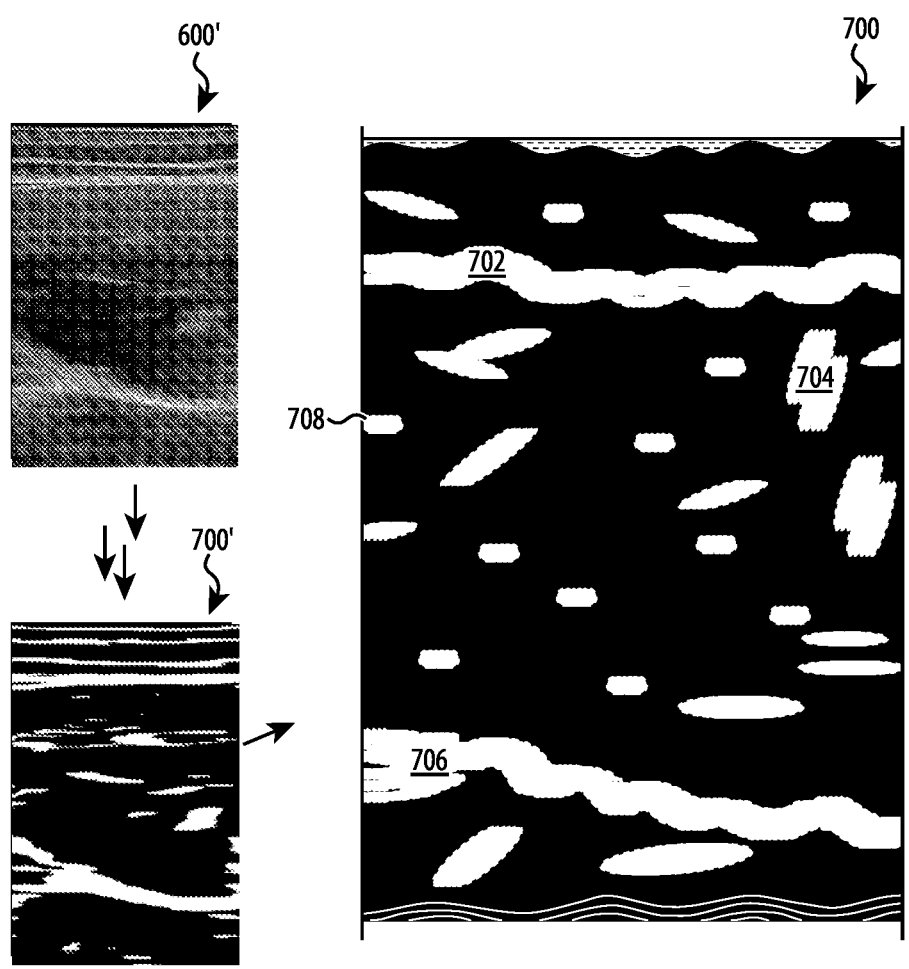
FIG. 7 depicts a conceptual illustration of a thresholded horizontally blurred image to provide a binary image in accordance with at least one embodiment.

Next, method 400 proceeds to threshold the pixels of the blurred (and/or otherwise noise-introduced) image 600 to either black or white to provide a binary image 700, block 406, as shown in FIG. 7. Conceptual binary image 700 corresponds generally to actual binary image 700'.

Thresholding is a method of image segmentation and is well known to those skilled in the art and need not be discussed in detail herein. A high level discussion of thresholding is provided so as to facilitate general understanding of the process so as to further appreciate the advantageous achievement of SNTA 100 and method 300. From a gray scale image, thresholding may be used to create a binary image, such as binary image 700 from blurred (and/or otherwise noise-introduced) scan image 600.

More specifically, each pixel of the blurred (and/or otherwise noise-introduced) scan image 600 has a value equal to or ranging from black (i.e., 0) to white (i.e., 255). To threshold the pixels, those above a midpoint (i.e., 127) are reset to white (i.e., 255) while those pixels at or below the midpoint (i.e., 127) are reset to black (i.e., 0). Of course this scale is merely exemplary and an alternative scale may be used. In addition, although color is the attribute for thresholding as described herein, in alternative embodiments thresholding may be applied to another color, luminance, darkness, contrast or other identifiable attribute of each pixel. Further, although thresholding is discussed using the midpoint, use of other threshold values is possible and contemplated. In various implementations, the threshold value may be set according to the particular apparatus used to obtain the image.

Moreover the present disclosure is further processing the scan image so as to provide a binary image that has only two possible values for each pixel. The remaining elements, of which elements 702, 704, 706 and 708 are exemplary, are crisp white elements with very discernable edges.

Next, method 400 proceeds to morph the remaining elements of the binary image 700 to remove small elements and connect large elements. To "morph" or "morphing" refers to mathematical morphology—a technique for the analysis and processing of geometric structures based on set theory, lattice theory, topology and or random functions and is a known technique applied to digital images. The basic morphological operators or morphological functions as they are also known are erosion, dilation, opening and closing. These morphological functions are well known to those skilled in the art and need not be discussed in detail herein.

A high level discussion of morphing, a.k.a. mathematical morphology, is provided so as to facilitate general understanding of the process so as to further appreciate the advantageous achievement of SNTA 100 and method 300.

The basic idea in binary morphology of a binary image is to probe an image with a simple, predefined shape such as a disc, square, cross or other simple geometric shape which is referred to as a structuring element and is itself a binary image. Opening removes white "holes" while closing removes black "holes." In accordance with at least one embodiment, the morphological function applied to further process the scan image so as to distinguish the muscle tissue size is the morphological function of opening.

Opening is obtained by eroding an image following by then dilating the image. The erosion of a binary image A (the binary image 700) by the structuring element B (a disc of radius r) in Euclidean space E=Rd is generally understood by the equation:

$$A \ominus B = \{z \varepsilon E | B_z \subset A\}$$

where Bz is the translation of B by the vector Z, i.e.:

$$B_z = \{b+z | b \varepsilon B\}, \forall z \varepsilon E.$$

When the structuring element B such as a square or disc has a center located on the origin E, the erosion of A by B can be understood as the locus of points reached by the center of B when B moves inside A.

The erosion of A by B is also given by the expression:

$$A \ominus B = \cap_{b \varepsilon B} A_{-b}.$$

The dilation of A by the structuring element B is defined by:

$$A \oplus B = \cup_{b \varepsilon B} A_b.$$

The dilation is commutative, also given by:

$$A \oplus DB = B \oplus A = \cup_{a \varepsilon A} B_a.$$

As before, when the structuring element B such as a square or disc has a center located on the origin E, the dilation of A by B can be understood as the locus of the points covered when the center of B moves inside A.

Figure 8:
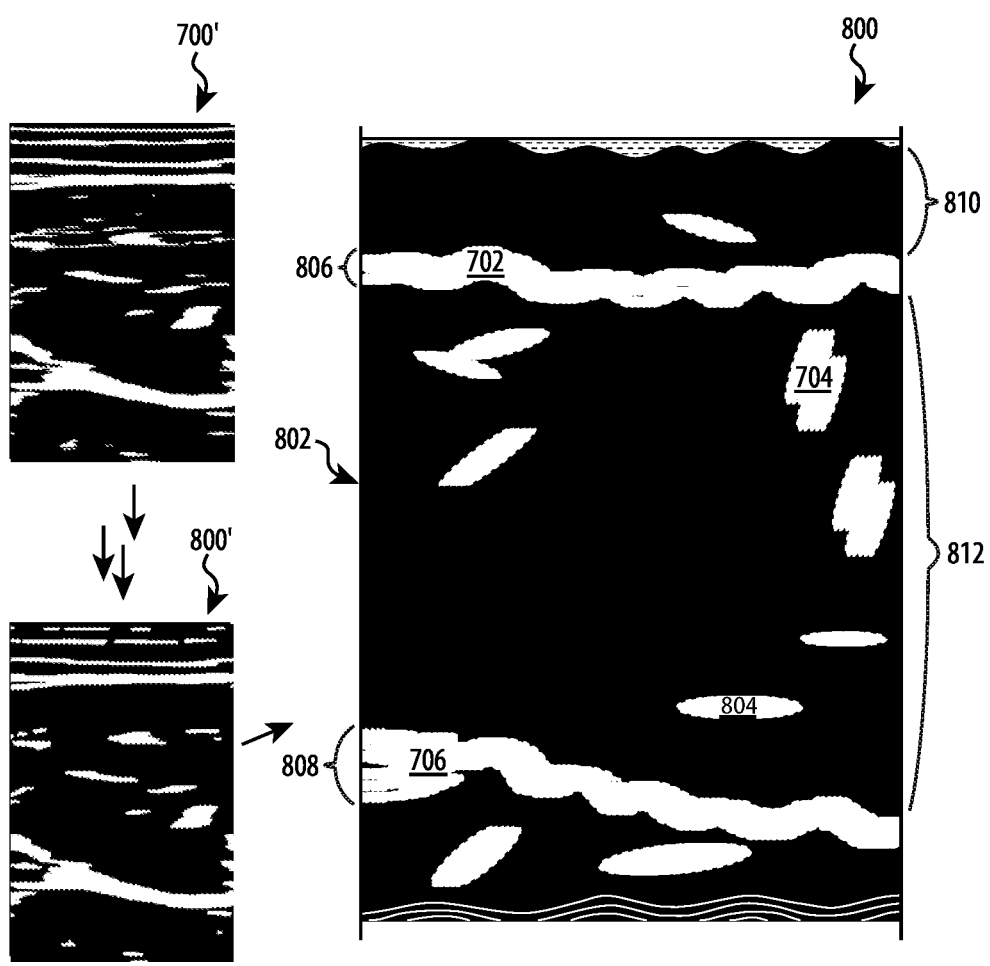
FIG. 8 depicts a conceptual illustration of a morphed image provided from the binary image in accordance with at least one embodiment.

More simply sated, for at least one embodiment the morphological function of opening is applied so as to further reduce the number of "white" elements within the binary image 700 so as to result in a reduced element image shown as morphed image 800, shown in FIG. 8. Again conceptual morphed image 800 corresponds generally to actual morphed image 800'.

Comparing morphed image 800 to binary image 700 it can and will be seen that the majority of smaller white elements, such as element 708 shown in FIG. 7, have been removed by the morphing process in providing morphed image 800.

With the elements of the processed binary image now further reduced it is quite clear that this morphed image 800 is distantly related to original scan image 200. However, because of the binary nature of morphed image 800 and the reduced number of elements, morphed image 800 is advantageously poised to permit the identification and distinguishing of a generally contiguous middle black element 802 within the morphed image 800, block 410.

For at least one embodiment, distinguishing the muscle tissue as the middle black element 802 from the remaining elements as asserted by block 410 is further understood and appreciated with respect to refinement 450. Moreover, an element such as exemplary element 804 is selected, block 452. For this selected element, one or more characteristics is determined, such as but not limited to area, center of mass, horizontal length, vertical height, etc. . . . It is understood and appreciated that the boundaries between different tissues is generally defined by fibrous tissues, which due to the above described image processing techniques have now evolved to being a generally continuous horizontal white band running generally continuously across the processed image.

Elements that do not have a horizontal length approaching the horizontal width of the processed image may generally be discounted and eliminated. Center of Mass and Area calculations may also be compared to reference expectations so as to further justify the elimination of all but the most likely bands defined by fibrous tissues.

Moreover, after determining one or more characteristics is determined for the selected element, method 450 continues with a query to determine if there are more elements remaining for analysis, decision 456. If there are indeed additional elements, a new element is elected, block 458 and the process returns to determining one or more characteristics for the new element, block 454.

When all of the elements have been evaluated, and the non-fibrous tissue elements generally eliminated, there are in general two generally horizontal, generally continuous white bands, of which white bands 806, 808 are exemplary, to be appreciated within the processed image, block 460. There may indeed be several horizontal white bands that, but the image processing as described above has evolved the scan image to such an extent that there are at least two prominent white bands which are both generally horizontal and generally continuous across the entire image. These prominent bands are readily distinguished over less prominent bands, such as by the calculations of center of mass, area, horizontal length and vertical height.

Because the muscle tissue 812 is developed between layers of other tissues, the muscle tissue may be distinguished to be the middle black layer 802 between the generally horizontal and horizontally continuous bands 806, 808. In other words the muscle tissue 812 is distinguished to be the tissue layer 802 between the generally horizontal white bands 806, 808 that are generally horizontally continuous across the morphed image 800, block 462.

Figure 9:
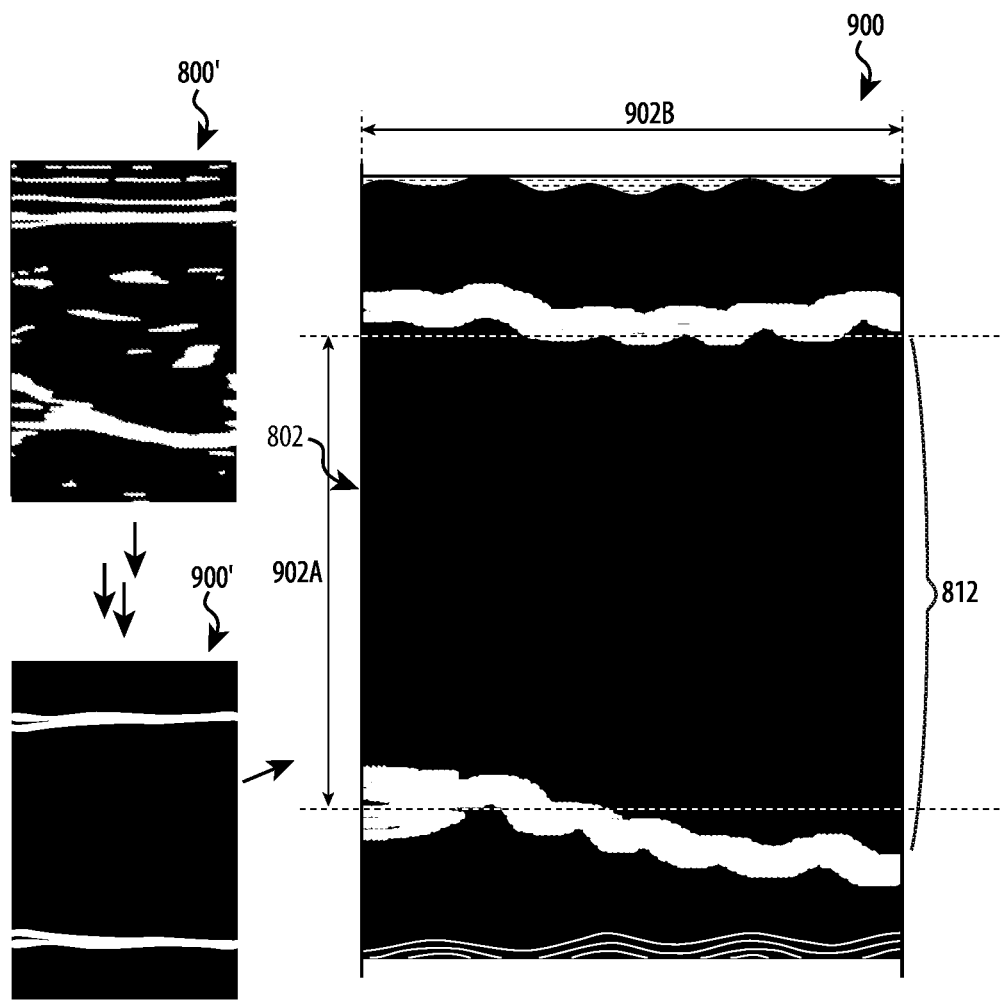
FIG. 9 depicts a conceptual illustration of the resulting processed image for non-invasive determination of human muscle tissue size in accordance with at least one embodiment.
Figure 10:
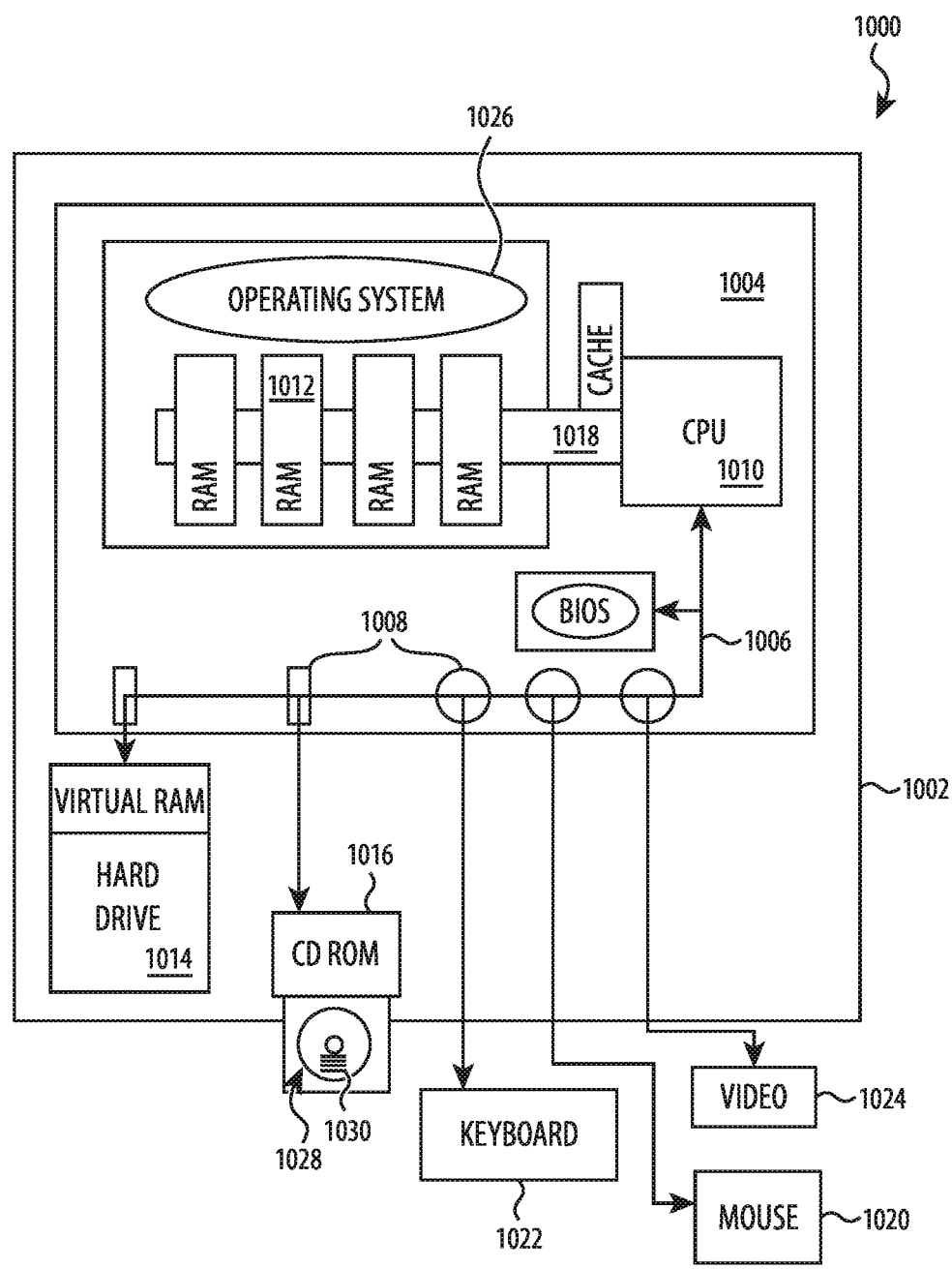
FIG. 10 depicts a block diagram of a computer system in accordance with at least one embodiment.

With the muscle tissue now distinguished, the non-relevant layers may be further removed, for the resulting highly processed image 900 shown in FIG. 9. Once again, conceptual processed image 900 corresponds generally to actual processed image 900'.

As the scan image is known to have a scale, a determination of the size for the distinguished muscle tissue 812 is now permitted with a high degree of precision using the thickness 902A, the cross-sectional area determinable from the thickness 902A and width 902B, and so on, block 412. As shown, in FIG. 9, for at least one embodiment of the present disclosure, this determination of muscle tissue size may account for the average size of the distinguished muscle tissue 812 as identified in processed image 900. For varying alternative embodiments, the muscle tissue size may be determined as the mean, median, mode, or midrange value. Further still a combination of these values may be returned to the operator for potentially a greater understanding and appreciation of the subject's muscle tissue size as determined for one or more areas of his or her body.

For example, a single thickness 902A measured at a single point across the distinguished muscle tissue 812 may be used to determine the muscle tissue size. It may be assumed that the single thickness 902A allows for an adequately accurate determination of muscle tissue size.

However, in other examples, a number of thicknesses 902A measured at various points across the distinguished muscle tissue 812 may be used to determine the muscle tissue size. In some implementations, these multiple thicknesses 902A may be averaged to determine the muscle tissue size. Such averaging may use the mean, median, mode, midrange value, and so on. This may provide a more accurate determination of muscle tissue size than measuring at only a single point. Increased accuracy may be achieved by considering an increasing number of thicknesses 902A.

In various other examples, the cross-sectional area of the muscle tissue 812 may be used to determine the muscle tissue size. The cross-sectional area may be determined by multiplying the thickness 902A by the width 902B. In some implementations, a more accurate cross-sectional area of the muscle tissue size may be determined by multiplying multiple thicknesses 902A measured at multiple points by multiple widths 902B measured at multiple points.

Although some of the above examples of determining the muscle tissue size have included elements such as elements 704 and 804, it is understood that these are examples. In various examples, the area of such non-muscle tissue elements may be determined and subtracted from the area of the muscle tissue 812 as part of determining the size of the muscle tissue. Various configurations are possible and contemplated without departing from the scope of the present disclosure.

In some implementations, a thickness measure may be ascertained. The thickness measurement may be used as a depiction of muscle size as opposed to a muscle area or other determinations. In such implementations, muscle area may still be calculated and used for various purposes. In some examples of such implementations, muscle area may be used as a scan quality measurement, as an additional metric to evaluate as part of muscle size determination, and so on.

In implementations where a thickness measure is ascertained and used as a depiction of muscle size, the thickness may be calculated in a variety of ways. In some examples, a center of mass of the identified muscle area in a vertical (with respect to the horizontal axis used to define a horizontal axis) direction may be determined. The thickness measure may then be determined to be double the center of mass of the identified muscle area in the vertical direction.

For example, in some implementations, the rectus formoris and the vastus lateralis may be identified in a subject's left and right legs. A thickness measurement may be obtained for each of the rectus formoris and the vastus lateralis in each of the subject's left and right legs by doubling the center of mass of each of the rectus formoris and the vastus lateralis in each of the subject's left and right legs in the vertical direction. These thickness measurements may then be presented (such as in millimeters). The thickness measurements may be presented along with other information, such as a percentage difference between the rectus formoris or the vastus lateralis in one leg compared to the other, a tracked percentage change in a respective rectus formoris or vastus lateralis from one or more previous measurements, a categorical rating (such as small, average, large as compared to data stored for other subjects in comparable categories such as similar body mass index, age, gender, a combination thereof, or the like), and so on.

A scan may include only a portion of a muscle tissue 812. As such, in some implementations, data regarding the muscle tissue determined from a scan may be correlated to tissue models in order to estimate the size of the entire muscle tissue, including both the portion within the scan and the portion not within the scan. In this way, a more accurate determination of muscle tissue size may be obtained.

Additionally, data determined from multiple scans may be combined. For example, multiple scans may each include a portion of a muscle tissue 812. As such, the muscle tissue 812 size determined using each scan may be combined in order to determine a total muscle tissue size.

Although refinement 450 is illustrated and described as distinguishing the muscle tissue 812 by identifying the generally horizontal and horizontally continuous bands 806, 808 and determining the tissue in the middle, it is understood that this is an example. In other implementations, other methods may be used to distinguish the muscle tissue without departing from the scope of the present disclosure.

For example, with reference again to FIG. 8, the muscle tissue 812 will be the largest element composed of contiguous pixels of the same value (i.e., black) in the morphed image 800 (body fat tissue 810 being the second largest as shown). Thus, in this example, the largest element composed of continuous black pixels in the morphed image 800 may be found and identified to distinguish the muscle tissue 812, regardless of any presence of determination of generally horizontal and horizontally continuous bands 806, 808.

In such a case, the difference between the minimum black pixel of the largest element composed of continuous black pixels in the morphed image 800 from the maximum (the furthest two black pixels apart in the largest element composed of continuous black pixels in the morphed image 800, such as the top left and bottom right pixels of the muscle tissue 812) may correspond to the thickness, or size, of the muscle tissue 812.

The element corresponding to the muscle tissue 812 may be considered to be composed of contiguous black values despite the presence of elements such as element 804 within it because the element corresponding to the muscle tissue 812 surrounds element 804. As such, the element corresponding to the muscle tissue 812 is still composed of contiguous black pixels even if elements such as element 804 not composed of black pixels are surrounded therewithin (the element corresponding to the muscle tissue 812 being completely separated from the black pixels corresponding to the body fat tissue 810 by the generally horizontal and horizontally continuous bands 806, 808, which are not surrounded therewithin).

By way of another example, three main layers may be identified from the morphed image 800. These may correspond to the body fat tissue 810, the muscle tissue 812, and the tissue below the muscle tissue 812 (such as bone, other muscle tissues, and so on). These three tissues may be separated by the generally horizontal and horizontally continuous bands 806, 808. Since it may be known that the muscle tissue 812 will be the middle layer, the three main layers may be identified from the morphed image 800 and the muscle tissue 812 distinguished based on its position in the three main layers.

To briefly summarize, for at least one embodiment the method of non-invasive determination of human muscle tissue includes receiving at least one ultrasound scan image (block 302) of at least a portion of a skin layer as disposed above one or more additional tissue layers, the skin layer defining a horizontal axis and the image provided by a plurality of pixels; introducing noise into the pixels of the image (block 404); thresholding the pixels of the image to provide a binary image having a plurality of structural elements of different sizes (block 406); morphing the structural elements of the binary image to remove small structural elements and connect large structural elements (block 408); distinguishing muscle tissue from remaining structural elements (block 410); and determining the muscle tissue size (412). The size may be an area of the muscle tissue, a thickness of the muscle tissue, a doubled center of mass of the muscle tissue in a vertical direction in relation to a horizontal axis defined by one or more skin layers, and so on.

With the muscle tissue size now determined, method 400 may return the determined muscle tissue size to the operator, block 416. Various information based upon the determined muscle tissue size may also be returned to the operator.

For example, a muscle tissue size rating may be returned to the operator. In some implementations, the muscle tissue size rating may involve a scale, such as a rating between "small" and "large," a value between 1 and 100, and so on. The muscle tissue size rating may be based on comparison of muscle tissue size to previously measured or a historical muscle tissue size (such as where analysis is repeated over time upon additional scan images to evaluate the muscle tissue size over time), comparison to other subjects (such as subjects with similar characteristics like age, gender, occupation, sport, and so on), comparison to one or more muscle tissue size goals (such as a performance objective to increase muscle tissue size, balance similar muscles, make a muscle sleeker, and so on), comparison to a similar muscle (such as the left bicep to the right bicep), comparison of contralateral muscles (such as by calculating the percent difference between the right and left contralateral muscles, calculating the percent difference between the two, tracking any improvement over time, categorizing if the percent difference is large/average/small, and so on), and so on. Any of this data to which the muscle tissue size may be compared may be retrieved from one or more storage medium in order for the comparison to be performed.

By way of another example, advice based on the muscle tissue size may also be returned to the operator. In some implementations, advice regarding training, food, and/or other parameters may be based on comparison of the muscle tissue size to a desired muscle tissue size or muscle tissue size goal. For example, advice regarding performance of specific exercises, additional weight or repetitions, increased or decreased protein, increased or decreased carbohydrates, and so on may be returned when the muscle tissue size is below the desired muscle tissue size or muscle tissue size goal, above the desired muscle tissue size or muscle tissue size goal, and so on. Specific advice to return based on the results of a comparison, as well as the comparison results under which to return such advice, may be may be retrieved from one or more storage medium.

The determination of muscle tissue size as provided by SNTA 100 and/or methods 300, 350 and 400 is applicable in a wide variety of qualified formulas for the determination of a number of different values which may be used by the subject or subject's doctor, trainer, caretaker, or other in a variety of different ways.

For example, a baseball trainer may utilize the above to determine the muscle tissue size to evaluate muscle tissue sizes of a batter who is attempting to increase muscle size to be able to hit further. The advice returned may compare the batter's muscle tissue sizes against previous determinations and/or other batters in the field, as well as indicate an adjusted training plan for the batter to maximize continued growth towards the batter's goal.

In yet another example, a medical professional may utilize the above to determine muscle tissue sizes of a patient who has been in traction in order to determine whether it is safe for the patient to attempt to walk unaided. Muscle tissues may atrophy while a patient is immobilized, and the patient may fall and seriously injure themselves anew if they attempt to walk unaided before their muscle tissues can support them. As such, the advice may indicate whether or not the patient's muscle tissue size has sufficiently developed to the point that it is safe for the patient to walk without the assistance of crutches or other devices.

In still another example, a football coach may utilize the above to determine muscle tissue sizes of a tight end. The advice may indicate that the tight end is increasing strength too much for a particular muscle tissue at the expense of speed and suggest an adjusted training plan for the tight end focusing more on aerobic exercise of the muscle and less on anaerobic, such as increased running and decreased weight lifting.

In yet another example, an Olympic swimmer may utilize the above to determine that the swimmer's right bicep is larger than the left. Imbalanced muscle tissue could cause the swimmer to pull one direction in the water and/or other performance issues. As such, the advice may indicate the imbalance and modify the swimmer's training schedule in order to correct the imbalance (such as by encouraging faster increase in the size of the left bicep, decreasing the speed at which the right bicep will increase in order to allow the left to catch up, allowing the size of the right bicep to decrease, and so on).

With respect to the above description of SNTA 100 and methods 300, 350 and 400, it is understood and appreciated that the method may be rendered in a variety of different forms of code and instruction as may be preferred for different computer systems and environments. To expand upon the initial suggestion of a processor based device such as a computer 114 shown in FIG. 1 and discussed above, FIG. 10 is a high-level block diagram of an example computer system 1000. Computer system 1000 has a case 1002, enclosing a main board 1004. The main board 1004 has a system bus 1006, connection ports 1008, a processing unit, such as Central Processing Unit (CPU) 1010 with at least one processor/microprocessor (not shown) and a memory storage device, such as main memory 1012, and optionally a solid state drive or hard drive 1014 and/or CD/DVD ROM drive 1016.

Memory bus 1018 couples main memory 1012 to CPU 1010. A system bus 1006 couples storage devices such as, but not limited to, hard drive 1014, CD/DVD ROM drive 1016 and connection ports 1008 to CPU 1010. Multiple input devices may be provided, such as for example a mouse 1020 and/or keyboard 1022. Multiple output devices may also be provided, such as for example a video display 1024 and a printer (not shown). In varying embodiments, the video display 1024 may also be a touch sensitive input device.

Computer system 1000 may be a commercially available system, such as a desktop workstation unit provided by IBM, Dell Computers, Gateway, Apple, Sun Microsystems, or other computer system provider. Computer system 1000 may also be a smart phone or tablet computer such as an iPhone or iPad provided by Apple, the HP Slate, the Augen or Archos Android tablets, the Motorola Xoom or other such device. Computer system 1000 may also be a networked computer system, wherein memory storage components such as hard drive 1014, additional CPUs 1010 and output devices such as printers are provided by physically separate computer systems commonly connected together in the network. Those skilled in the art will understand and appreciate that physical composition of components and component interconnections comprising computer system 1000, and select a computer system 1200 suitable for the schedules to be established and maintained.

When computer system 1000 is activated, an operating system 1026 may load into main memory 1012 as part of the boot strap startup sequence and ready the computer system 1000 for operation. At the simplest level, and in the most general sense, the tasks of an operating system may fall into specific categories—process management, device management (including application and user interface management) and memory management.

In such a computer system 1000, the CPU 1010 may be operable to perform one or more of the methods of non-invasive determination of muscle tissue size as described above. Those skilled in the art will understand that a computer-readable medium 1028 on which is a computer program 1030 for non-invasive determination of muscle tissue size may be provided to the computer system 1000. The form of the medium 1028 and language of the program 1030 are understood to be appropriate for computer system 1000. Utilizing the memory stores, such as for example one or more hard drives 1014 and main memory 1012, the operable CPU 1010 will read the instructions provided by the computer program 1030 and operate to perform as SNTA 100 as described above.

To summarize, for at least one embodiment, a system for a non-invasive system of determining muscle tissue size is provided by a processing unit; a memory storage device coupled to the processing unit; the processing unit being adapted to: receive at least one ultrasound scan image of at least a portion of a skin layer as disposed above one or more additional tissue layers, the skin layer defining a horizontal axis and the image provided by a plurality of pixels; introduce noise into the pixels of the image; threshold the pixels of the image to provide a binary image having a plurality of structural elements of different sizes; morph the structural elements of the binary image to remove small structural elements and connect large structural elements; distinguish muscle tissue from remaining structural elements; and determine the muscle tissue size.

Figure 11:
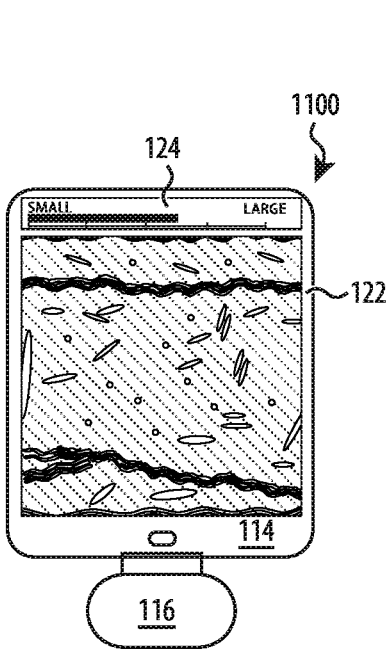
FIG. 11 depicts a conceptual illustration of a first alternative configuration for a system for non-invasive tissue evaluation that may be used to determine human muscle tissue size in accordance with at least one embodiment.

With respect to the various forms of the processor based device, such as the computer 114, further discussed and described as computer system 1000, FIGS. 11-16 present alternative embodiments for the structural arrangement of components comprising SNTA 100. More specifically, for alternative SNTA 1100 as shown in FIG. 11, the ultrasound transducer 116 is coupled directly to the computer 114, such that SNTA 1100 is itself disposed adjacent to the target tissue 108 (not shown).

Figure 12:
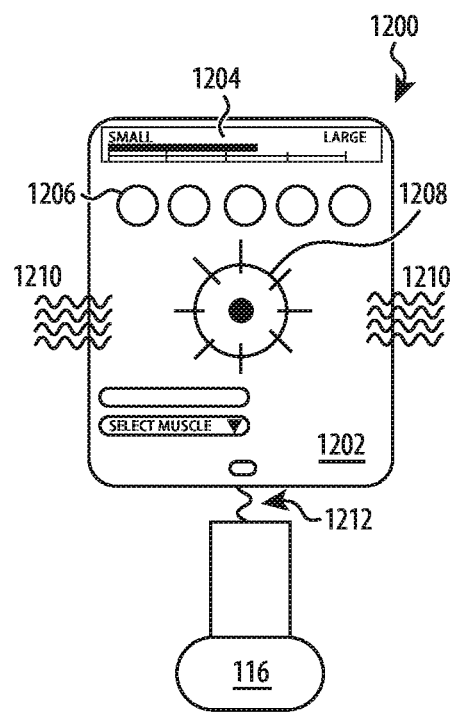
FIG. 12 depicts a conceptual illustration of a second alternative configuration for a system for non-invasive tissue evaluation that may be used to determine human muscle tissue size in accordance with at least one embodiment.
Figure 13:
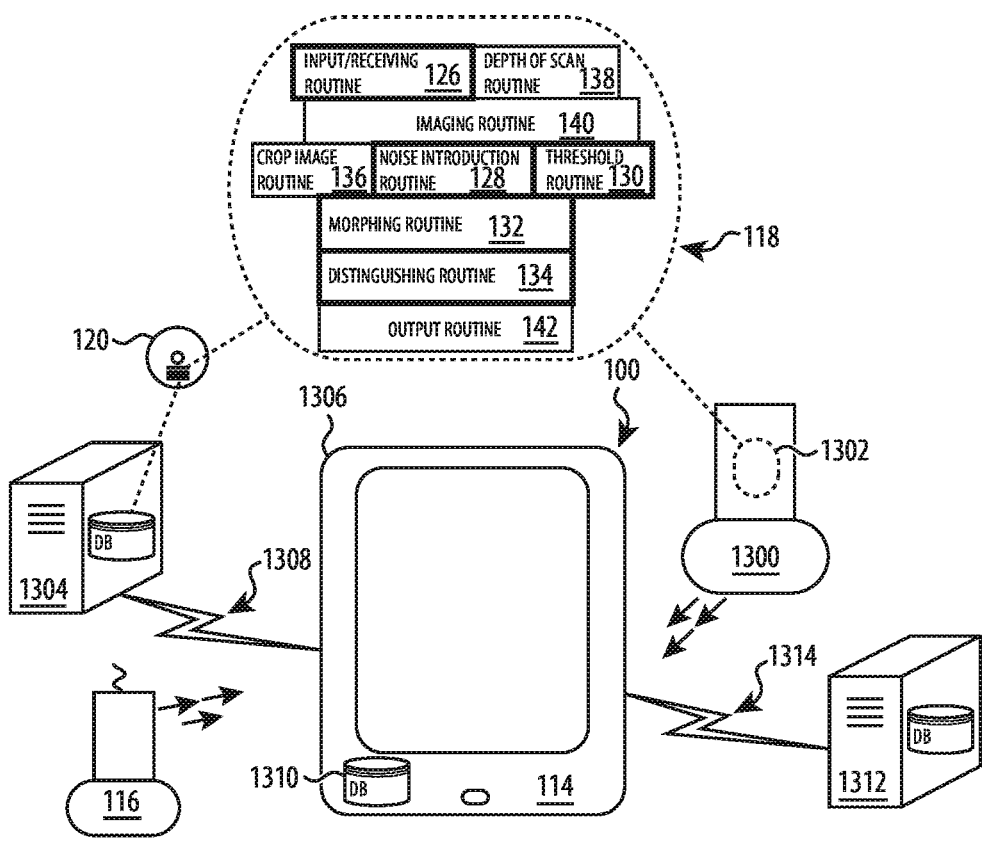
FIG. 13 depicts a conceptual illustration of a third alternative configuration for a system for non-invasive tissue evaluation that may be used to determine human muscle tissue size in accordance with at least one embodiment.

For alternative SNTA 1200 shown as FIG. 12, a dedicated processor based device such as a customized computer 1202 is provided, as opposed to adapting a pre-existing smart phone, tablet computer or other computer system. For SNTA 1200, the display 122 of SNTA 1200 is not shown so as to illustrate that alternative output devices such as an indicator 1204, lights 1206, speaker 1208, vibrator 1210 and/or combinations thereof can provide an operator with an indication of the non-invasively determined muscle tissue size. As with SNTA 1100, the ultrasound transducer 116 may be directly coupled to the customized computer 1202, or tethered by a communications link 1212—wireless or wired as shown.

Further, for yet other embodiments, the computer program 118 to adapt a computer 114 may be provided directly by enhanced ultrasound transducer 1300. More specifically, the computer program 118 may be incorporated as part of the circuit structure 1302 of enhanced ultrasound transducer 1300 such that upon connection to the computer 114, SNTA 100 is provided.

As suggested above with respect to FIG. 1, the computer program 118 may also be provided by a non-portable media such as a disc 120 to a third party computer, such as computer 1304, providing an application platform such as but not limited to the Apple App Store. A user can then connect his or her computer 114, such as tablet computer 1306 to the third party computer 1304 by a network 1308 (wired or wireless) or other communication channel and obtain computer program 118 so as to adapt his or her computer 1306 to perform as SNTA 100 when a scan of a target muscle is provided.

In varying embodiments, this scan may be provided by coupling computer 1306 to ultrasound transducer 116 operated as described above, receiving a scan of a target muscle from internal storage 1310, or receiving a scan of a target muscle from another computer system 1312 via wired or wireless network 1314, or other appropriate communication channel.

Figure 14:
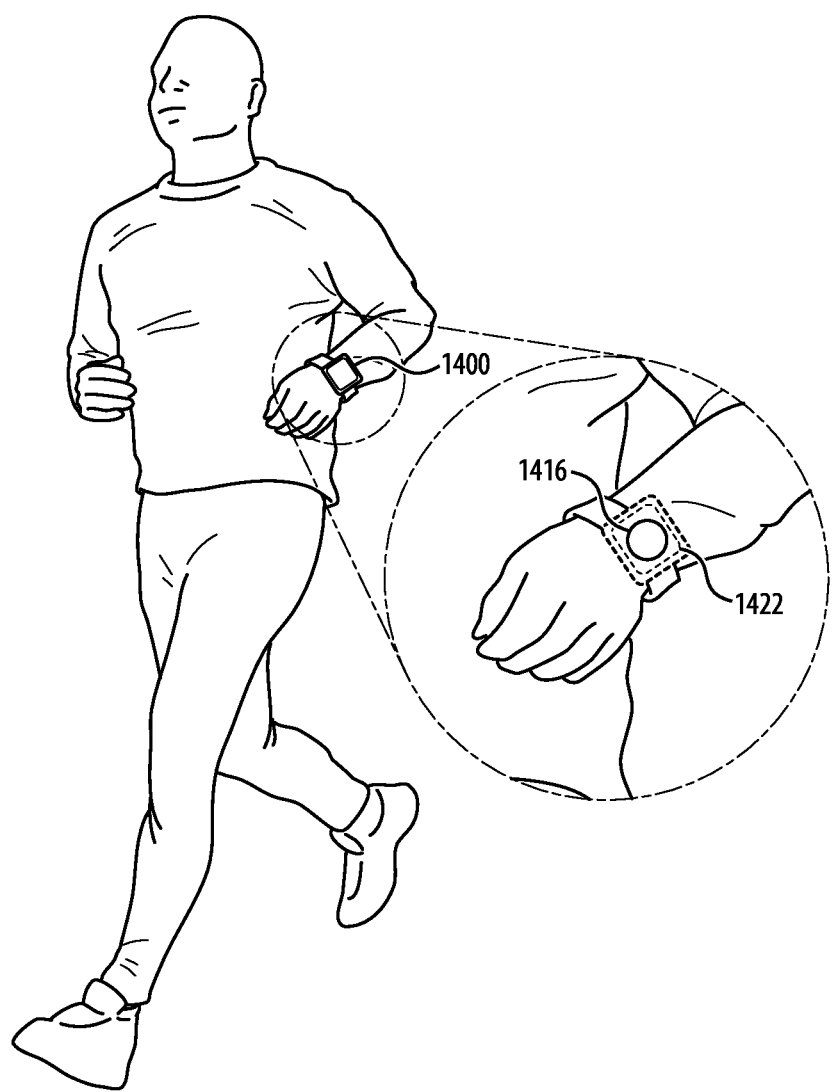
FIG. 14 depicts a conceptual illustration of a fourth alternative configuration for a system for non-invasive tissue evaluation that may be used to determine human muscle tissue size in accordance with at least one embodiment.

As shown in FIG. 14, in some embodiments, the SNTA 1400 may be a wearable device, such as a smart watch or other device operable to couple around a user's body part. The SNTA 1400 may include a transducer 1416 positioned adjacent the user in order to obtain scans and/or other data at a variety of different times, such as during a user's workout. The SNTA 1400 may also include a display 1422 for providing real time and/or other analysis information to the user.

Figure 15:
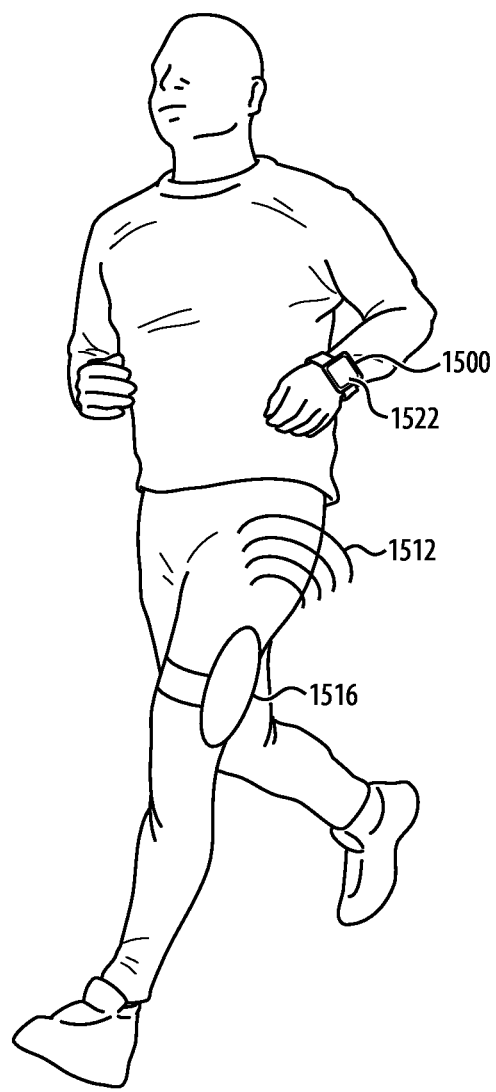
FIG. 15 depicts a conceptual illustration of a fifth alternative configuration for a system for non-invasive determination of human muscle tissue size in accordance with at least one embodiment.

As shown in FIG. 15, in other embodiments, a wearable SNTA 1500 may be used with a separately wearable transducer 1516. In this way, the SNTA 1500 may be coupled around one body part while the transducer 1516 obtains one or more scans related to tissues located in another body part. The SNTA 1500 may receive data regarding such scans from the transducer 1516, such as wirelessly 1512, and provide real time and/or other analysis information to the user via a display 1522.

Figure 16:
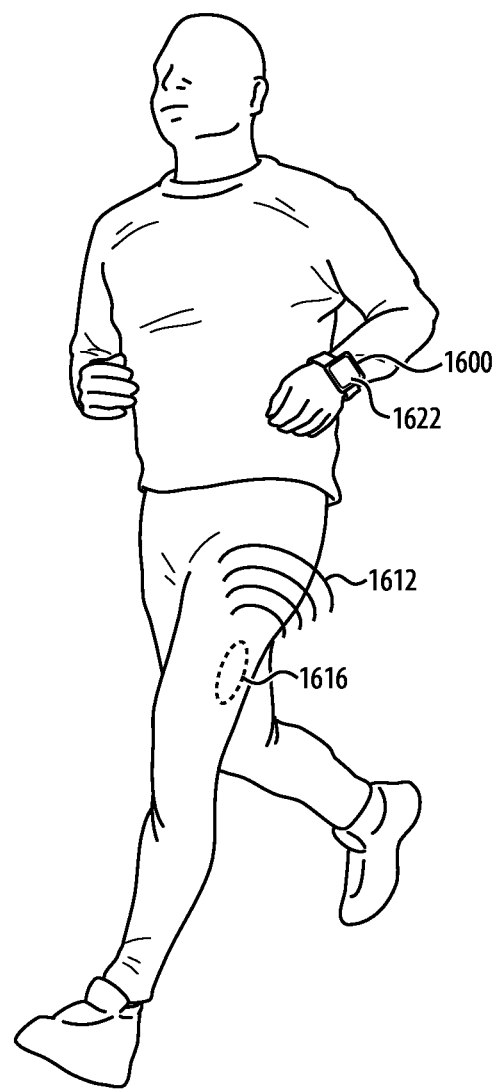
FIG. 16 depicts a conceptual illustration of a sixth alternative configuration for a system for non-invasive determination of human muscle tissue size in accordance with at least one embodiment.

As shown in FIG. 16, in still other embodiments, a wearable SNTA 1600 may be used with a transducer implant 1616 located inside the user's body. In this way, the SNTA 1600 may obtain one or more scans related to tissues located in the body without requiring attachment and positioning of a transducer for use. The SNTA 1600 may receive data regarding such scans from the transducer implant 1616, such as wirelessly 1612, and provide real time and/or other analysis information to the user via a display 1622.

To summarize, for at least one embodiment, the present disclosure is provided upon a non-transitory machine readable medium on which is stored a computer program comprising instructions to adapt a computer system having a processor to permit non-invasive determination of human muscle tissue size. This computer program includes computer executable instructions to provide a receiving routine operatively associated with an input device for receiving at least one ultrasound scan image of at least a portion of a skin layer as disposed above one or more additional tissue layers, the skin layer defining a horizontal axis and the image provided by a plurality of pixels; a noise introduction routine for introducing noise into the pixels of the image; a thresholding routine for thresholding the pixels of the image to provide a binary image having a plurality of structural elements of different sizes; a morphing routine for morphing the structural elements of the binary image to remove small structural elements and connect large structural elements; and a distinguishing routine for distinguishing muscle tissue from remaining structural elements and determining the muscle tissue size.

Changes may be made in the above methods, systems and structures without departing from the scope hereof. It should thus be noted that the matter contained in the above description and/or shown in the accompanying drawings should be interpreted as illustrative and not in a limiting sense. The following claims are intended to cover all generic and specific features described herein, as well as all statements of the scope of the present method, system and structure, which, as a matter of language, might be said to fall therebetween.

In the present disclosure, the methods disclosed may be implemented as sets of instructions or software readable by a device. Further, it is understood that the specific order or hierarchy of steps in the methods disclosed are examples of sample approaches. In other embodiments, the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may take the form of, but is not limited to, a magnetic storage medium (e.g., floppy diskette, video cassette, and so on); optical storage medium (e.g., CD-ROM); magneto-optical storage medium; read only memory (ROM); random access memory (RAM); erasable programmable memory (e.g., EPROM and EEPROM); flash memory; and so on.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A non-invasive method of muscle tissue analysis, comprising:
    receiving an ultrasound scan image of at least a portion of a skin layer as disposed above one or more additional tissue layers;
    morphing the ultrasound scan image to generate a morphed image by removing or joining elements of the ultrasound scan image;
    determining muscle tissue size using the morphed image; and
    determining a numeric muscle tissue size rating at least by comparing the muscle tissue size to a goal.

2. The method of claim 1, wherein the goal is a muscle tissue size goal.

3. The method of claim 1, wherein the goal is based on a historic muscle tissue size.

4. The method of claim 1, wherein the goal is based on muscle tissue sizes of other subjects.

5. The method of claim 1, wherein the goal is based on a comparison of contralateral muscles.

6. The method of claim 1, wherein the goal is based on a performance objective.

7. The method of claim 1, wherein morphing the ultrasound scan image aids in distinguishing muscle tissue from remaining structural elements.

8. A non-invasive method of muscle tissue analysis, comprising:
    morphing an ultrasound scan image of at least a portion of a skin layer as disposed above one or more additional tissue layers to generate a morphed image by removing or joining elements of the ultrasound scan image;
    distinguishing muscle tissue from remaining structural elements in the morphed image; and
    determining a numeric muscle tissue size rating at least by comparing muscle tissue size to a goal.

9. The method of claim 8, wherein the muscle tissue is partially present in the ultrasound scan image.

10. The method of claim 8, wherein:
    a first dimension of the muscle tissue is partially present in the ultrasound scan image; and
    a second dimension of the muscle tissue is fully present in the ultrasound scan image.

11. The method of claim 10, wherein:
    the first dimension is a horizontal dimension; and
    the second dimension is a vertical dimension.

12. The method of claim 8, wherein the processing includes introducing noise into pixels of the ultrasound scan image.

13. The method of claim 8, wherein the processing includes thresholding pixels of the ultrasound scan image to provide a binary image having structural elements of different sizes.

14. The method of claim 13, wherein the processing further includes morphing the structural elements of the binary image to remove small structural elements and connect large structural elements.

15. A non-invasive method of muscle tissue analysis, comprising:
    obtaining an ultrasound scan image;
    processing the ultrasound scan image by at least distinguishing muscle tissue from remaining structural elements by identifying the muscle tissue as a largest element composed of contiguous pixels having a same value;
    determining muscle tissue size using the ultrasound scan image after processing; and
    determining a numeric muscle tissue size rating at least by comparing the muscle tissue size to a goal.

16. The method of claim 15, wherein the processing further includes introducing noise into pixels of the ultrasound scan image.

17. The method of claim 15, further comprising reporting the muscle tissue size.

18. The method of claim 15, further comprising reporting the numeric muscle tissue size rating.

19. The method of claim 15, wherein the goal comprises an objective to balance similar muscles.

20. The method of claim 15, wherein the goal comprises an objective to make a muscle slimmer or more toned.

* * * * *